United States Patent
Yin et al.

(10) Patent No.: US 12,269,890 B2
(45) Date of Patent: Apr. 8, 2025

(54) HUMANIZED ANTI-HUMAN OX40 MONOCLONAL ANTIBODY, PREPARATION METHOD THEREFOR AND USE THEREOF

(71) Applicant: Nanjing GenScript Biotech Co., Ltd., Nanjing (CN)

(72) Inventors: Liusong Yin, Nanjing (CN); Tielin Zhou, Singapore (SG); Xinpo Jiang, Vancouver (CA); Zhuo Fang, Nanjing (CN); Yanling Mi, Nanjing (CN); Chunchen Wu, Nanjing (CN)

(73) Assignee: NANJING GENSCRIPT BIOTECH CO., LTD., Jiangsu (CN)

( * ) Notice: Subject to any disclaimer, the term of this patent is extended or adjusted under 35 U.S.C. 154(b) by 959 days.

(21) Appl. No.: 17/297,386

(22) PCT Filed: Nov. 26, 2019

(86) PCT No.: PCT/CN2019/120808
§ 371 (c)(1),
(2) Date: May 26, 2021

(87) PCT Pub. No.: WO2020/108463
PCT Pub. Date: Jun. 4, 2020

(65) Prior Publication Data
US 2022/0119540 A1    Apr. 21, 2022

(30) Foreign Application Priority Data
Nov. 26, 2018 (CN) .......................... 201811420381.3

(51) Int. Cl.
*C07K 16/28* (2006.01)

(52) U.S. Cl.
CPC ...... *C07K 16/2878* (2013.01); *C07K 2317/24* (2013.01); *C07K 2317/33* (2013.01); *C07K 2317/565* (2013.01); *C07K 2317/92* (2013.01)

(58) Field of Classification Search
None
See application file for complete search history.

(56) References Cited

FOREIGN PATENT DOCUMENTS

| CN | 109232738 A | * | 1/2019 | ......... | C07K 16/2878 |
|---|---|---|---|---|---|
| WO | WO 2015/153513 A1 | | 10/2015 | | |
| WO | WO 2015/153513 A8 | | 10/2015 | | |
| WO | WO 2016/057667 A1 | | 4/2016 | | |
| WO | WO 2017/021910 A1 | | 2/2017 | | |

OTHER PUBLICATIONS

Owens et al. Nat Rev Drug Disc. 2007. 6, 187 (Year: 2007).*
Vajdos et al. J Mol Biol. Jul. 5, 2002;320(2):415-28 (Year: 2002).*
Rudikoff et al. Proc Natl Acad Sci. 1982. 79: 1979-1983.) (Year: 1982).*
Bedouelle et al. FEES J. Jan. 2006;273(1):34-46 (Year: 2006).*
CN 109232738 A English Translation (Year: 2019).*
Williams et al. 2010. Antibody Engineering Ch. 21: Humanising Antibodies by CDR Grafting. Springer Protocols. DOI: 10.1007/978-3-642-01144-3_21 (Year: 2010).*
International Search Report and Written Opinion mailed on Feb. 19, 2020 for International Application No. PCT/CN2019/120808 (7 pages).
English translation of International Search Report mailed on Feb. 19, 2020 for International Application No. PCT/CN2019/120808 (2 pages).
Supplementary European Search Report mailed on Dec. 2, 2022 in European Application No. 19891274.3 (10 pages).

* cited by examiner

*Primary Examiner* — Daniel E Kolker
*Assistant Examiner* — Brianna K Swartwout
(74) *Attorney, Agent, or Firm* — Klarquist Sparkman, LLP

(57) ABSTRACT

The present invention relates to a humanized anti-human OX40 monoclonal antibody, and a preparation method and use thereof. The humanized anti-human OX40 monoclonal antibody provided in the present invention has high affinity and specificity for OX40, and can stimulate T cells to secrete cytokines, for example, specifically activate the positive immune regulation by OX40 and activate T cells to secrete cytokines. Therefore, the functional humanized anti-human OX40 monoclonal antibody provided in the present invention activates T cells by activating the OX40 signaling pathway, thereby achieving the purpose of tumor immunotherapy.

15 Claims, 13 Drawing Sheets
Specification includes a Sequence Listing.

SEQUENCE LISTING

<160> NUMBER OF SEQ ID NOS: 42

<210> SEQ ID NO 1
<211> LENGTH: 117
<212> TYPE: PRT

```
<213> ORGANISM: Artificial Sequence
<220> FEATURE:
<223> OTHER INFORMATION: 99A2A8D4E8 -VH

<400> SEQUENCE: 1

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Ser Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Lys Asn Leu Lys Asn Glu Asp Thr Ala Ser Tyr Phe Cys
                85                  90                  95

Ala Arg Val Arg Pro Trp Tyr Leu Ala Val Trp Gly Ala Gly Thr Thr
            100                 105                 110

Val Thr Val Ser Ser
            115

<210> SEQ ID NO 2
<211> LENGTH: 107
<212> TYPE: PRT
<213> ORGANISM: Artificial Sequence
<220> FEATURE:
<223> OTHER INFORMATION: 99A2A8D4E8 -VL

<400> SEQUENCE: 2

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Tyr Ser Gly Val Pro Ser Arg Phe Ser Gly
    50                  55                  60

Ser Gly Ser Gly Ala Asp Tyr Ser Leu Thr Val Ser Asn Leu Glu Gln
65                  70                  75                  80

Glu Asp Ile Ala Thr Tyr Phe Cys Gln Gln Ala Asn Thr Leu Pro Leu
                85                  90                  95

Thr Phe Gly Ala Gly Thr Lys Leu Glu Leu Lys
            100                 105

<210> SEQ ID NO 3
<211> LENGTH: 117
<212> TYPE: PRT
<213> ORGANISM: Artificial Sequence
<220> FEATURE:
<223> OTHER INFORMATION: 99A2A8D4E8-VH-GRAFTED

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Arg Leu Glu Trp Met
        35                  40                  45
```

```
Gly Trp Ile Ser Thr Glu Thr Gly Glu Pro Thr Tyr Ala Asp Asp Phe
            50                  55                  60

Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Val Arg Pro Trp Tyr Leu Ala Val Trp Gly Gln Gly Thr Leu
                100                 105                 110

Val Thr Val Ser Ser
            115

<210> SEQ ID NO 4
<211> LENGTH: 107
<212> TYPE: PRT
<213> ORGANISM: Artificial Sequence
<220> FEATURE:
<223> OTHER INFORMATION: 99A2A8D4E8-VL-GRAFTED

<400> SEQUENCE: 4

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Tyr Thr Ser Arg Leu Tyr Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Ala Asn Thr Leu Pro Leu
                 85                  90                  95

Thr Phe Gly Gly Gly Thr Lys Leu Glu Ile Lys
                100                 105

<210> SEQ ID NO 5
<211> LENGTH: 117
<212> TYPE: PRT
<213> ORGANISM: Artificial Sequence
<220> FEATURE:
<223> OTHER INFORMATION: 99A2A8D4E8-VH-CBM

<400> SEQUENCE: 5

Gln Val Gln Leu Val Gln Ser Gly Pro Glu Val Lys Lys Pro Gly Ala
  1               5                  10                  15

Ser Val Lys Ile Ser Cys Lys Ala Ser Gly Tyr Thr Phe Thr Asp Tyr
                 20                  25                  30

Ser Met His Trp Val Lys Gln Ala Pro Gly Gln Gly Leu Glu Trp Met
             35                  40                  45

Gly Trp Ile Ser Thr Glu Thr Gly Glu Pro Thr Tyr Ala Asp Asp Phe
 50                  55                  60

Lys Gly Arg Phe Thr Phe Thr Leu Asp Thr Ser Ala Ser Thr Ala Tyr
 65                  70                  75                  80

Leu Glu Ile Ser Ser Leu Arg Ser Glu Asp Thr Ala Val Tyr Phe Cys
                 85                  90                  95
```

```
Ala Arg Val Arg Pro Trp Tyr Leu Ala Val Trp Gly Gln Gly Thr Leu
            100                 105                 110

Val Thr Val Ser Ser
        115

<210> SEQ ID NO 6
<211> LENGTH: 107
<212> TYPE: PRT
<213> ORGANISM: Artificial Sequence
<220> FEATURE:
<223> OTHER INFORMATION: 99A2A8D4E8-VL-CBM

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu Tyr Ser Gly Val Pro Ser Arg Phe Ser Gly
50                  55                  60

Ser Gly Ser Gly Thr Asp Tyr Thr Leu Thr Val Ser Ser Leu Gln Pro
65                  70                  75                  80

Glu Asp Ile Ala Thr Tyr Phe Cys Gln Gln Ala Asn Thr Leu Pro Leu
                85                  90                  95

Thr Phe Gly Gly Gly Thr Lys Leu Glu Ile Lys
            100                 105

<210> SEQ ID NO 7
<211> LENGTH: 117
<212> TYPE: PRT
<213> ORGANISM: Artificial Sequence
<220> FEATURE:
<223> OTHER INFORMATION: AH02906-VH

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Lys Gln Ala Pro Gly Gln Gly Leu Glu Trp Met
        35                  40                  45

Gly Trp Ile Ser Thr Glu Thr Gly Glu Pro Thr Tyr Ala Asp Asp Phe
50                  55                  60

Lys Gly Arg Phe Thr Ile Thr Leu Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Arg Pro Trp Tyr Leu Ala Val Trp Gly Gln Gly Thr Leu
            100                 105                 110

Val Thr Val Ser Ser
        115

<210> SEQ ID NO 8
<211> LENGTH: 117
<212> TYPE: PRT
<213> ORGANISM: Artificial Sequence
<220> FEATURE:
<223> OTHER INFORMATION: AH02913-VH
```

<400> SEQUENCE: 8

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Lys Gln Ala Pro Gly Gln Gly Leu Glu Trp Met
        35                  40                  45

Gly Trp Ile Ser Thr Glu Thr Gly Glu Pro Thr Tyr Ala Asp Asp Phe
    50                  55                  60

Lys Gly Arg Val Thr Ile Thr Leu Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Val Arg Pro Trp Tyr Leu Ala Val Trp Gly Gln Gly Thr Leu
            100                 105                 110

Val Thr Val Ser Ser
        115

<210> SEQ ID NO 9
<211> LENGTH: 117
<212> TYPE: PRT
<213> ORGANISM: Artificial Sequence
<220> FEATURE:
<223> OTHER INFORMATION: AH02915-VH

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Lys Gln Ala Pro Gly Gln Gly Leu Glu Trp Met
        35                  40                  45

Gly Trp Ile Ser Thr Glu Thr Gly Glu Pro Thr Tyr Ala Asp Asp Phe
    50                  55                  60

Lys Gly Arg Val Thr Ile Thr Leu Asp Thr Ser Ala Ser Thr Ala Tyr
65                  70                  75                  80

Leu Glu Ile Ser Ser Leu Arg Ser Glu Asp Thr Ala Val Tyr Tyr Cys
                85                  90                  95

Ala Arg Val Arg Pro Trp Tyr Leu Ala Val Trp Gly Gln Gly Thr Leu
            100                 105                 110

Val Thr Val Ser Ser
        115

<210> SEQ ID NO 10
<211> LENGTH: 117
<212> TYPE: PRT
<213> ORGANISM: Artificial Sequence
<220> FEATURE:
<223> OTHER INFORMATION: AH02916-VH

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Lys Gln Ala Pro Gly Gln Gly Leu Glu Trp Met
        35                  40                  45

Gly Trp Ile Ser Thr Glu Thr Gly Glu Pro Thr Tyr Ala Asp Asp Phe
            50                  55                  60

Lys Gly Arg Val Thr Ile Thr Leu Asp Thr Ser Ala Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Val Arg Pro Trp Tyr Leu Ala Val Trp Gly Gln Gly Thr Leu
            100                 105                 110

Val Thr Val Ser Ser
            115

<210> SEQ ID NO 11
<211> LENGTH: 117
<212> TYPE: PRT
<213> ORGANISM: Artificial Sequence
<220> FEATURE:
<223> OTHER INFORMATION: AH02917-VH

<400> SEQUENCE: 11

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
             20                  25                  30

Ser Met His Trp Val Lys Gln Ala Pro Gly Gln Gly Leu Glu Trp Met
         35                  40                  45

Gly Trp Ile Ser Thr Glu Thr Gly Glu Pro Thr Tyr Ala Asp Asp Phe
     50                  55                  60

Lys Gly Arg Phe Thr Ile Thr Leu Asp Thr Ser Ala Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Val Arg Pro Trp Tyr Leu Ala Val Trp Gly Gln Gly Thr Leu
            100                 105                 110

Val Thr Val Ser Ser
            115

<210> SEQ ID NO 12
<211> LENGTH: 117
<212> TYPE: PRT
<213> ORGANISM: Artificial Sequence
<220> FEATURE:
<223> OTHER INFORMATION: AH02919-VH

<400> SEQUENCE: 12

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
             20                  25                  30

Ser Met His Trp Val Lys Gln Ala Pro Gly Gln Gly Leu Glu Trp Met
         35                  40                  45

Gly Trp Ile Ser Thr Glu Thr Gly Glu Pro Thr Tyr Ala Asp Asp Phe
     50                  55                  60

Lys Gly Arg Val Thr Ile Thr Arg Asp Thr Ser Ala Ser Thr Ala Tyr
 65                  70                  75                  80

Leu Glu Ile Ser Ser Leu Arg Ser Glu Asp Thr Ala Val Tyr Phe Cys
                 85                  90                  95

```
Ala Arg Val Arg Pro Trp Tyr Leu Ala Val Trp Gly Gln Gly Thr Leu
            100                 105                 110

Val Thr Val Ser Ser
        115

<210> SEQ ID NO 13
<211> LENGTH: 117
<212> TYPE: PRT
<213> ORGANISM: Artificial Sequence
<220> FEATURE:
<223> OTHER INFORMATION: AH02921-VH

<400> SEQUENCE: 13

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Glu Trp Met
        35                  40                  45

Gly Trp Ile Ser Thr Glu Thr Gly Glu Pro Thr Tyr Ala Asp Asp Phe
    50                  55                  60

Lys Gly Arg Phe Thr Ile Thr Leu Asp Thr Ser Ala Ser Thr Ala Tyr
65                  70                  75                  80

Leu Glu Ile Ser Ser Leu Arg Ser Glu Asp Thr Ala Val Tyr Phe Cys
                85                  90                  95

Ala Arg Val Arg Pro Trp Tyr Leu Thr Val Trp Gly Gln Gly Thr Leu
            100                 105                 110

Val Thr Val Ser Ser
        115

<210> SEQ ID NO 14
<211> LENGTH: 117
<212> TYPE: PRT
<213> ORGANISM: Artificial Sequence
<220> FEATURE:
<223> OTHER INFORMATION: AH02922-VH

<400> SEQUENCE: 14

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Ser Met His Trp Val Arg Gln Ala Pro Gly Gln Arg Leu Glu Trp Met
        35                  40                  45

Gly Trp Ile Ser Thr Glu Thr Gly Glu Pro Thr Tyr Ala Asp Asp Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Arg Pro Trp Tyr Leu Val Val Trp Gly Gln Gly Thr Leu
            100                 105                 110

Val Thr Val Ser Ser
        115

<210> SEQ ID NO 15
<211> LENGTH: 117
<212> TYPE: PRT
```

<213> ORGANISM: Artificial Sequence
<220> FEATURE:
<223> OTHER INFORMATION: AH02923-VH

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ser Met His Trp Val Arg Gln Ala Pro Gly Gln Gly Leu Glu Trp Met
            35                  40                  45

Gly Trp Ile Ser Thr Glu Thr Gly Glu Pro Thr Tyr Ala Asp Asp Phe
    50                  55                  60

Lys Gly Arg Phe Thr Phe Thr Leu Asp Thr Ser Ala Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Val Arg Pro Trp Tyr Leu Ala Val Trp Gly Gln Gly Thr Leu
            100                 105                 110

Val Thr Val Ser Ser
        115

<210> SEQ ID NO 16
<211> LENGTH: 117
<212> TYPE: PRT
<213> ORGANISM: Artificial Sequence
<220> FEATURE:
<223> OTHER INFORMATION: AH02925-VH

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ser Met His Trp Val Lys Gln Ala Pro Gly Gln Gly Leu Glu Trp Met
            35                  40                  45

Gly Trp Ile Ser Thr Glu Thr Gly Glu Pro Thr Tyr Ala Asp Asp Phe
    50                  55                  60

Lys Gly Arg Val Thr Ile Thr Arg Asp Thr Ser Ala Ser Thr Ala Tyr
65                  70                  75                  80

Leu Glu Ile Ser Ser Leu Arg Ser Glu Asp Thr Ala Val Tyr Phe Cys
                85                  90                  95

Ala Arg Val Arg Pro Trp Tyr Leu Ala Val Trp Gly Gln Gly Thr Leu
            100                 105                 110

Val Thr Val Ser Ser
        115

<210> SEQ ID NO 17
<211> LENGTH: 107
<212> TYPE: PRT
<213> ORGANISM: Artificial Sequence
<220> FEATURE:
<223> OTHER INFORMATION: AH02906-VL

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Tyr Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Ile Ala Thr Tyr Phe Cys Gln Gln Ala Asn Thr Leu Pro Leu
                 85                  90                  95

Thr Phe Gly Gly Gly Thr Lys Leu Glu Ile Lys
            100                 105

<210> SEQ ID NO 18
<211> LENGTH: 107
<212> TYPE: PRT
<213> ORGANISM: Artificial Sequence
<220> FEATURE:
<223> OTHER INFORMATION: AH02913-VL

<400> SEQUENCE: 18

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
                 20                  25                  30

Leu Asn Trp Tyr Gln Gln Lys Pro Gly Lys Ala Val Lys Leu Leu Ile
            35                  40                  45

Tyr Tyr Thr Ser Arg Leu Tyr Ser Gly Val Pro Ser Arg Phe Ser Gly
 50                  55                  60

Ser Gly Ser Gly Thr Asp Tyr Thr Phe Thr Ile Ser Ser Leu Gln Pro
 65                  70                  75                  80

Glu Asp Ile Ala Thr Tyr Phe Cys Gln Gln Ala Asn Thr Leu Pro Leu
                 85                  90                  95

Thr Phe Gly Gly Gly Thr Lys Leu Glu Ile Lys
            100                 105

<210> SEQ ID NO 19
<211> LENGTH: 107
<212> TYPE: PRT
<213> ORGANISM: Artificial Sequence
<220> FEATURE:
<223> OTHER INFORMATION: AH02915-VL

<400> SEQUENCE: 19

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
                 20                  25                  30

Leu Asn Trp Tyr Gln Gln Lys Pro Gly Lys Ala Pro Lys Leu Leu Ile
            35                  40                  45

Tyr Tyr Thr Ser Arg Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Ile Ala Thr Tyr Phe Cys Gln Gln Ala Asn Thr Leu Pro Leu
                 85                  90                  95

Thr Phe Gly Gly Gly Thr Lys Leu Glu Ile Lys
            100                 105

```
<210> SEQ ID NO 20
<211> LENGTH: 107
<212> TYPE: PRT
<213> ORGANISM: Artificial Sequence
<220> FEATURE:
<223> OTHER INFORMATION: AH02916-VL

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu Tyr Ser Gly Val Pro Ser Arg Phe Ser Gly
50                  55                  60

Ser Gly Ser Gly Thr Asp Tyr Thr Phe Thr Ile Ser Ser Leu Gln Pro
65                  70                  75                  80

Glu Asp Ile Ala Thr Tyr Phe Cys Gln Gln Ala Asn Thr Leu Pro Leu
                85                  90                  95

Thr Phe Gly Gly Gly Thr Lys Leu Glu Ile Lys
            100                 105

<210> SEQ ID NO 21
<211> LENGTH: 107
<212> TYPE: PRT
<213> ORGANISM: Artificial Sequence
<220> FEATURE:
<223> OTHER INFORMATION: AH02917-VL

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Ala Asn Thr Leu Pro Leu
                85                  90                  95

Thr Phe Gly Gly Gly Thr Lys Leu Glu Ile Lys
            100                 105

<210> SEQ ID NO 22
<211> LENGTH: 107
<212> TYPE: PRT
<213> ORGANISM: Artificial Sequence
<220> FEATURE:
<223> OTHER INFORMATION: AH02919-VL

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Val Lys Leu Leu Ile
        35                  40                  45
```

```
Tyr Tyr Thr Ser Arg Leu Tyr Ser Gly Val Pro Ser Arg Phe Ser Gly
         50                  55                  60

Ser Gly Ser Gly Thr Asp Tyr Thr Leu Thr Ile Ser Ser Leu Gln Pro
 65                  70                  75                  80

Glu Asp Ile Ala Thr Tyr Tyr Cys Gln Gln Ala Asn Thr Leu Pro Leu
                 85                  90                  95

Thr Phe Gly Gly Gly Thr Lys Leu Glu Ile Lys
            100                 105

<210> SEQ ID NO 23
<211> LENGTH: 107
<212> TYPE: PRT
<213> ORGANISM: Artificial Sequence
<220> FEATURE:
<223> OTHER INFORMATION: AH02921-VL

<400> SEQUENCE: 23

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Tyr Thr Ser Arg Leu Tyr Ser Gly Val Pro Ser Arg Phe Ser Gly
         50                  55                  60

Ser Gly Ser Gly Thr Asp Tyr Thr Leu Thr Ile Ser Ser Leu Gln Pro
 65                  70                  75                  80

Glu Asp Ile Ala Thr Tyr Phe Cys Gln Gln Ala Asn Thr Leu Pro Leu
                 85                  90                  95

Thr Phe Gly Gly Gly Thr Lys Leu Glu Ile Lys
            100                 105

<210> SEQ ID NO 24
<211> LENGTH: 107
<212> TYPE: PRT
<213> ORGANISM: Artificial Sequence
<220> FEATURE:
<223> OTHER INFORMATION: AH02922-VL

<400> SEQUENCE: 24

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Tyr Thr Ser Arg Leu Tyr Ser Gly Val Pro Ser Arg Phe Ser Gly
         50                  55                  60

Ser Gly Ser Gly Thr Asp Tyr Thr Leu Thr Ile Ser Ser Leu Gln Pro
 65                  70                  75                  80

Glu Asp Ile Ala Thr Tyr Tyr Cys Gln Gln Ala Asn Thr Leu Pro Leu
                 85                  90                  95

Thr Phe Gly Gly Gly Thr Lys Leu Glu Ile Lys
            100                 105

<210> SEQ ID NO 25
<211> LENGTH: 107
<212> TYPE: PRT
```

```
<213> ORGANISM: Artificial Sequence
<220> FEATURE:
<223> OTHER INFORMATION: AH02923-VL

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu Tyr Ser Gly Val Pro Ser Arg Phe Ser Gly
50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Ala Asn Thr Leu Pro Leu
                85                  90                  95

Thr Phe Gly Gly Gly Thr Lys Leu Glu Ile Lys
            100                 105

<210> SEQ ID NO 26
<211> LENGTH: 107
<212> TYPE: PRT
<213> ORGANISM: Artificial Sequence
<220> FEATURE:
<223> OTHER INFORMATION: AH02925-VL

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Ala Asn Thr Leu Pro Leu
                85                  90                  95

Thr Phe Gly Gly Gly Thr Lys Leu Glu Ile Lys
            100                 105

<210> SEQ ID NO 27
<211> LENGTH: 5
<212> TYPE: PRT
<213> ORGANISM: Artificial Sequence
<220> FEATURE:
<223> OTHER INFORMATION: HCDR1

<400> SEQUENCE: 27

Asp Tyr Ser Met His
1               5

<210> SEQ ID NO 28
<211> LENGTH: 17
<212> TYPE: PRT
<213> ORGANISM: Artificial Sequence
<220> FEATURE:
<223> OTHER INFORMATION: HCDR2
```

```
<400> SEQUENCE: 28

Trp Ile Ser Thr Glu Thr Gly Glu Pro Thr Tyr Ala Asp Asp Phe Lys
1               5                   10                  15
Gly

<210> SEQ ID NO 29
<211> LENGTH: 8
<212> TYPE: PRT
<213> ORGANISM: Artificial Sequence
<220> FEATURE:
<223> OTHER INFORMATION: HCDR3

<400> SEQUENCE: 29

Val Arg Pro Trp Tyr Leu Ala Val
1               5

<210> SEQ ID NO 30
<211> LENGTH: 11
<212> TYPE: PRT
<213> ORGANISM: Artificial Sequence
<220> FEATURE:
<223> OTHER INFORMATION: LCDR1

<400> SEQUENCE: 30

Arg Ala Ser Gln Asp Ile Ser Asn Tyr Leu Asn
1               5                   10

<210> SEQ ID NO 31
<211> LENGTH: 7
<212> TYPE: PRT
<213> ORGANISM: Artificial Sequence
<220> FEATURE:
<223> OTHER INFORMATION: LCDR2

<400> SEQUENCE: 31

Tyr Thr Ser Arg Leu Tyr Ser
1               5

<210> SEQ ID NO 32
<211> LENGTH: 9
<212> TYPE: PRT
<213> ORGANISM: Artificial Sequence
<220> FEATURE:
<223> OTHER INFORMATION: LCDR3

<400> SEQUENCE: 32

Gln Gln Ala Asn Thr Leu Pro Leu Thr
1               5

<210> SEQ ID NO 33
<211> LENGTH: 11
<212> TYPE: PRT
<213> ORGANISM: Artificial Sequence
<220> FEATURE:
<223> OTHER INFORMATION: MS Peptide fragment C1-2

<400> SEQUENCE: 33

Asp Ile Gln Met Thr Gln Ser Pro Ser Ser Leu
1               5                   10

<210> SEQ ID NO 34
<211> LENGTH: 8
<212> TYPE: PRT
<213> ORGANISM: Artificial Sequence
<220> FEATURE:
<223> OTHER INFORMATION: MS Peptide fragment C18-19
```

```
<400> SEQUENCE: 34

Phe Cys Ala Arg Val Arg Pro Trp
1               5

<210> SEQ ID NO 35
<211> LENGTH: 15
<212> TYPE: PRT
<213> ORGANISM: Artificial Sequence
<220> FEATURE:
<223> OTHER INFORMATION: MS Peptide fragment C15-18

<400> SEQUENCE: 35

Met Glu Leu Ser Ser Leu Arg Ser Glu Asp Thr Ala Val Tyr Phe
1               5                   10                  15

<210> SEQ ID NO 36
<211> LENGTH: 13
<212> TYPE: PRT
<213> ORGANISM: Artificial Sequence
<220> FEATURE:
<223> OTHER INFORMATION: MS Peptide fragment C71-72 or C73-74

<400> SEQUENCE: 36

Ser Cys Ser Val Met His Glu Ala Leu His Asn His Tyr
1               5                   10

<210> SEQ ID NO 37
<211> LENGTH: 7
<212> TYPE: PRT
<213> ORGANISM: Artificial Sequence
<220> FEATURE:
<223> OTHER INFORMATION: MS Peptide fragment C19 or C21

<400> SEQUENCE: 37

Cys Ala Arg Val Arg Pro Trp
1               5

<210> SEQ ID NO 38
<211> LENGTH: 6
<212> TYPE: PRT
<213> ORGANISM: Artificial Sequence
<220> FEATURE:
<223> OTHER INFORMATION: MS peptide fragment C15-16

<400> SEQUENCE: 38

Met Glu Leu Ser Ser Leu
1               5

<210> SEQ ID NO 39
<211> LENGTH: 24
<212> TYPE: PRT
<213> ORGANISM: Artificial Sequence
<220> FEATURE:
<223> OTHER INFORMATION: MS peptide fragment C42-43

<400> SEQUENCE: 39

Met Ile Ser Arg Thr Pro Glu Val Thr Cys Val Val Val Asp Val Ser
1               5                   10                  15

His Glu Asp Pro Glu Val Lys Phe
            20

<210> SEQ ID NO 40
<211> LENGTH: 11
<212> TYPE: PRT
<213> ORGANISM: Artificial Sequence
```

```
<220> FEATURE:
<223> OTHER INFORMATION: MS peptide fragment C41-42

<400> SEQUENCE: 40

Phe Pro Pro Lys Pro Lys Asp Thr Leu Met Ile
1               5                   10

<210> SEQ ID NO 41
<211> LENGTH: 14
<212> TYPE: PRT
<213> ORGANISM: Artificial Sequence
<220> FEATURE:
<223> OTHER INFORMATION: MS peptide fragment C6-8

<400> SEQUENCE: 41

Val Arg Gln Ala Pro Gly Gln Gly Leu Glu Trp Met Gly Trp
1               5                   10

<210> SEQ ID NO 42
<211> LENGTH: 10
<212> TYPE: PRT
<213> ORGANISM: Artificial Sequence
<220> FEATURE:
<223> OTHER INFORMATION: MS Peptide fragment T91-93

<400> SEQUENCE: 42

Asn Gln Val Ser Leu Thr Cys Leu Val Lys
1               5                   10
```

HUMANIZED ANTI-HUMAN OX40 MONOCLONAL ANTIBODY, PREPARATION METHOD THEREFOR AND USE THEREOF

CROSS REFERENCE TO RELATED APPLICATIONS

This is the U.S. National Stage of International Application No. PCT/CN2019/120808, filed Nov. 26, 2019, which was published in Chinese under PCT Article 21(2), which in turn claims the benefit of Chinese Patent Application No. 201811420381.3, filed on Nov. 26, 2018.

BACKGROUND

Technical Field

The present invention relates to the field of tumor immunotherapy and molecular immunology, and particularly to a humanized anti-human OX40 monoclonal antibody. The present invention also relates to a preparation method and use of the humanized anti-human OX40 monoclonal antibody.

Related Art

In the treatment of tumors, tumor immunotherapy is widely used. It has become the third important means of treatment besides radiotherapy and chemotherapy in tumor treatment, and has gradually become popular.

The immune system is a defense system in the host. To function normally, the immune system needs be able to sensitively detect the invasion of foreign pathogens and distinguish them from the own healthy tissues of an organism. Tumor immunotherapy takes advantage of this feature and regulates the function of immune cells in human body to allow human T cells to better recognize and act on cancerous cells, thereby eliminating pathological tissues.

The vertebrate immune system is a functional system composed of various organs, tissues, cells and molecules. It is the most potent mechanism for an organism to defend against the invasion of foreign substances. These immune organs, tissues, cells and molecules cooperate with each other to check and balance each other, so as to protect the organism against external infections and maintain homeostasis. Cellular immunity results from recognition by T cell receptor (TCR) of antigens presented by the major histocompatibility complex (MHC) on antigen presenting cells (APC), which is the first signal of T cell activation. However, T cell activation cannot be achieved merely by means of the first signal. It also requires an antigen independent second signal. The second signal is achieved through the interaction between a receptor or ligand on the surface of T cells and a corresponding costimulatory factor from APCs. Such mutual cooperation and mutual check and balance require the coordination and participation of many immune checkpoint proteins. Stimulatory immune checkpoint proteins can enhance the defense response of the immune system, and inhibitory immune checkpoint proteins can suppress an overly strong immune system to prevent the autoimmune response. During the development of therapeutic agents for immune checkpoint proteins, agonists or agonistic antibodies need to be developed for stimulatory immune checkpoint proteins, and inhibitors or inhibitory antibodies need to be developed for inhibitory immune checkpoint proteins.

There are many studies on inhibitory immune checkpoint proteins, such as PD-1 and CTLA-4. The antibody-mediated antagonism against the inhibitory immune checkpoint protein can inhibit the immune checkpoint pathway to enhance the function of T cells to kill tumor cells. However, for the vast majority of patients with cancers, regulation of inhibitory immune checkpoint proteins is not enough to eliminate tumors. To enhance the function of T cells to kill tumor cells, it is necessary not only to weaken the inhibitory pathway of T cells but also to strengthen the activation pathway of T cells. T cells activation requires participation of stimulatory immune checkpoint proteins, including 4-1BB, GITR and OX40. Through intracellular signal transduction, stimulatory immune checkpoint proteins can activate PKB/AKT, NF-kB, NFAT and other pathways to promote the expansion of and the production of cytokines by helper CD4+ T cells and cytotoxic CD8+ T cells, thereby improving the ability of the immune system to combat tumors.

OX40 (CD134; TNFRSF4) is mainly expressed on the surface of activated T cells, such as CD4, CD8 T cells, helper T cells (Th1, Th2, Th17), and CD4+Foxp3+ regulatory T cells; and also lowly expressed on natural killer cells (NK), natural killer T cells (NKT) and neutrophils. Unlike CD28 and CD27, it is not expressed in unactivated T cells. OX40 and its ligand OX40L (CD252) are both members of the tumor necrosis factor superfamily, and belong to the same large family as 4-1BB, CD27, CD40, and GITR, etc. OX40/OX40L is a second costimulatory immune checkpoint molecule, which participates in the activation, proliferation and survival of T cells, and plays a key role in the formation of germinal centers and the differentiation and maturation of dendritic cells.

The present invention provides a stimulatory antibody to OX40 to enhance the immune response of T cells to various antigens in tumor immunotherapy.

SUMMARY

The present invention provides a humanized anti-human OX40 monoclonal antibody or a functional fragment thereof, which comprises a heavy chain variable region and a light chain variable region, where the heavy chain variable region comprises amino acid sequences having a substitution(s), insertion(s) or deletion(s) of 1, 2, or 3 amino acid residues respectively in the following HCDR1, HCDR2, and HCDR3 sequences, and the light chain variable region comprises amino acid sequences having a substitution(s), insertion(s) or deletion(s) of 1, 2, or 3 amino acid residues respectively in the following LCDR1, LCDR2 and LCDR3 sequences:

HCDR1 having an amino acid sequence of DYSMH (SEQ ID NO: 27);
HCDR2 having an amino acid sequence of WISTETGEP-TYADDFKG (SEQ ID NO: 28);
HCDR3 having an amino acid sequence of VRPWYLAV (SEQ ID NO: 29);
LCDR1 having an amino acid sequence of RASQDIS-NYLN (SEQ ID NO: 30);
LCDR2 having an amino acid sequence of YTSRLYS (SEQ ID NO: 31); and
LCDR3 having an amino acid sequence of QQANTLPLT (SEQ ID NO: 32).

In one aspect, the present invention provides a humanized anti-human OX40 monoclonal antibody or a functional fragment thereof, which comprises a heavy chain variable region and a light chain variable region, where the heavy chain variable region comprises amino acid sequences having at least 80% identity respectively to the following HCDR1, HCDR2 and HCDR3 sequences, and the light chain variable region comprises amino acid sequences having at least 80% identity respectively to the following LCDR1, LCDR2 and LCDR3 sequences:

HCDR1 having an amino acid sequence of DYSMH (SEQ ID NO: 27);
HCDR2 having an amino acid sequence of WISTETGEP-TYADDFKG (SEQ ID NO: 28);
HCDR3 having an amino acid sequence of VRPWYLAV (SEQ ID NO: 29);
LCDR1 having an amino acid sequence of RASQDIS-NYLN (SEQ ID NO: 30);
LCDR2 having an amino acid sequence of YTSRLYS (SEQ ID NO: 31); and
LCDR3 having an amino acid sequence of QQANTLPLT (SEQ ID NO: 32).

In an embodiment, the heavy chain variable region comprises amino acid sequences having at least 81%, 82%, 83%, 84%, 85%, 86%, 87%, 88%, 89%, 90%, 91%, 92%, 93%, 94%, 95%, 96%, 97%, 98% or 99% identity respectively to the HCDR1, HCDR2 and HCDR3 sequences.

In an embodiment, the light chain variable region comprises amino acid sequences having at least 81%, 82%, 83%, 84%, 85%, 86%, 87%, 88%, 89%, 90%, 91%, 92%, 93%, 94%, 95%, 96%, 97%, 98% or 99% identity respectively to the LCDR1, LCDR2 and LCDR3 sequences.

In an embodiment, the present invention provides a humanized anti-human OX40 monoclonal antibody or a functional fragment thereof, which comprises a heavy chain variable region and a light chain variable region, where the heavy chain variable region comprises amino acid sequences as shown in the following HCDR1, HCDR2 and HCDR3 sequences, and the light chain variable region comprises amino acid sequences as shown in the following LCDR1, LCDR2 and LCDR3 sequences:

HCDR1 having an amino acid sequence of DYSMH (SEQ ID NO: 27);
HCDR2 having an amino acid sequence of WISTETGEP-TYADDFKG (SEQ ID NO: 28);
HCDR3 having an amino acid sequence of VRPWYLAV (SEQ ID NO: 29);
LCDR1 having an amino acid sequence of RASQDIS-NYLN (SEQ ID NO: 30);
LCDR2 having an amino acid sequence of YTSRLYS (SEQ ID NO: 31); and
LCDR3 having an amino acid sequence of QQANTLPLT (SEQ ID NO: 32).

In an embodiment, the amino acid sequence of the heavy chain variable region is selected from SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15 or SEQ ID NO: 16.

In an embodiment, the amino acid sequence of the light chain variable region is selected from SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 or SEQ ID NO: 26.

In an embodiment, the humanized anti-human OX40 monoclonal antibody or a functional fragment thereof has a heavy chain variable region and a light chain variable region selected from a combination of a heavy chain variable region as shown in SEQ ID NO: 7 and a light chain variable region as shown in SEQ ID NO: 17;
a heavy chain variable region as shown in SEQ ID NO: 8 and a light chain variable region as shown in SEQ ID NO: 18;
a heavy chain variable region as shown in SEQ ID NO: 9 and a light chain variable region as shown in SEQ ID NO: 19;
a heavy chain variable region as shown in SEQ ID NO: 10 and a light chain variable region as shown in SEQ ID NO: 20;
a heavy chain variable region as shown in SEQ ID NO: 11 and a light chain variable region as shown in SEQ ID NO: 21;
a heavy chain variable region as shown in SEQ ID NO: 12 and a light chain variable region as shown in SEQ ID NO: 22
a heavy chain variable region as shown in SEQ ID NO: 13 and a light chain variable region as shown in SEQ ID NO: 23;
a heavy chain variable region as shown in SEQ ID NO: 14 and a light chain variable region as shown in SEQ ID NO: 24;
a heavy chain variable region as shown in SEQ ID NO: 15 and a light chain variable region as shown in SEQ ID NO: 25; or
a heavy chain variable region as shown in SEQ ID NO: 16 and a light chain variable region as shown in SEQ ID NO: 26.

In a preferred embodiment, the humanized anti-human OX40 monoclonal antibody or a functional fragment thereof has a heavy chain variable region and a light chain variable region selected from a combination of a heavy chain variable region as shown in SEQ ID NO: 8 and a light chain variable region as shown in SEQ ID NO: 18;
a heavy chain variable region as shown in SEQ ID NO: 10 and a light chain variable region as shown in SEQ ID NO: 20;
a heavy chain variable region as shown in SEQ ID NO: 12 and a light chain variable region as shown in SEQ ID NO: 22
a heavy chain variable region as shown in SEQ ID NO: 13 and a light chain variable region as shown in SEQ ID NO: 23; or
a heavy chain variable region as shown in SEQ ID NO: 15 and a light chain variable region as shown in SEQ ID NO: 25.

In a further preferred embodiment, the humanized anti-human OX40 monoclonal antibody or a functional fragment thereof has a heavy chain variable region and a light chain variable region selected from a combination of a heavy chain variable region as shown in SEQ ID NO: 12 and a light chain variable region as shown in SEQ ID NO: 22; or
a heavy chain variable region as shown in SEQ ID NO: 13 and a light chain variable region as shown in SEQ ID NO: 23.

In an embodiment, the humanized anti-human OX40 monoclonal antibody of the present invention or a functional fragment thereof has a dissociation constant KD less than 3 nM.

In an embodiment, the humanized anti-human OX40 monoclonal antibody of the present invention or a functional fragment thereof specifically activates the positive immune regulation by OX40 and activates T cells to secrete cytokines.

In an embodiment, the present invention provides an isolated polynucleotide, which encodes the humanized anti-human OX40 monoclonal antibody of the present invention or a functional fragment thereof.

In an embodiment, the polynucleotide comprises a heavy chain coding sequence encoding the heavy chain variable region of the humanized anti-human OX40 monoclonal antibody of the present invention, and a light chain coding sequence encoding the light chain variable region of the humanized anti-human OX40 monoclonal antibody of the present invention.

In another aspect, the present invention provides an expression vector comprising the polynucleotide.

In another aspect, the present invention provides a host cell comprising the expression vector.

In an embodiment, the host cell is HEK293-6E cells.

In another aspect, the present invention provides use of the humanized anti-human OX40 monoclonal antibody or a functional fragment thereof, the polynucleotide, the expression vector or the host cell for the preparation of an anti-tumor drug.

In another aspect, the present invention provides use of the humanized anti-human OX40 monoclonal antibody or a functional fragment thereof, the polynucleotide, the expression vector or the host cell for the treatment of tumors.

In another aspect, the present invention provides the humanized anti-human OX40 monoclonal antibody or a functional fragment thereof, the polynucleotide, the expression vector or the host cell useful in the treatment of tumors.

In another aspect, the present invention provides an anti-tumor pharmaceutical composition, which comprises an effective amount of the humanized anti-human OX40 monoclonal antibody or a functional fragment thereof, and a pharmaceutically acceptable carrier.

In another aspect, the present invention provides a method for preparing the humanized anti-human OX40 monoclonal antibody or a functional fragment thereof, which comprises
(1) humanizing the murine antibody, and obtaining variable region coding sequences of the light chain and the heavy chain of the humanized anti-human OX40 monoclonal antibody or a functional fragment thereof; and
(2) using the variable region coding sequences in recombinant antibody production to obtain the functional humanized anti-human OX40 monoclonal antibody or a functional fragment thereof.

The humanized anti-human OX40 monoclonal antibody provided in the present invention has high affinity and specificity for OX40, and can stimulate T cells to secrete cytokines, for example, specifically activate the positive immune regulation by OX40 and activate T cells to secrete cytokines. Therefore, the functional humanized anti-human OX40 monoclonal antibody provided in the present invention activates T cells by activating the OX40 signaling pathway, thereby achieving the purpose of tumor immunotherapy.

BRIEF DESCRIPTION OF THE DRAWINGS

FIGS. 3A-3B show the determination of cross reactivity between humanized anti-human OX40 monoclonal antibodies and human/monkey OX-40 protein overexpressed on the cell surface, in which FIG. 3A shows the interaction between each monoclonal antibody and human OX-40 protein utilizing an ELISA assay; and FIG. 3B shows the interaction between each monoclonal antibody and monkey OX-40 protein utilizing an ELISA assay;

DETAILED DESCRIPTION

Figure 1A:
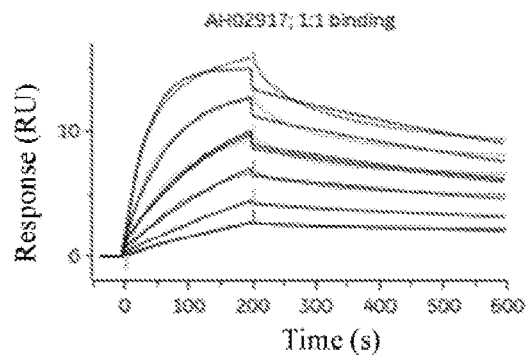
FIGS. 1A-1K show the affinity determination of humanized anti-human OX40 monoclonal antibodies, including specifically: AH02906 (FIG. 1A), AH02913 (FIG. 1B), AH02915 (FIG. 1C), AH02916 (FIG. 1D), AH02917 (FIG. 1E), AH02919 (FIG. 1F), AH02921 (FIG. 1G), AH02922 (FIG. 1H), AH02923 (FIG. 1I), AH02925 (FIG. 1J), and chimeric antibody (FIG. 1K).
Figure 1B:
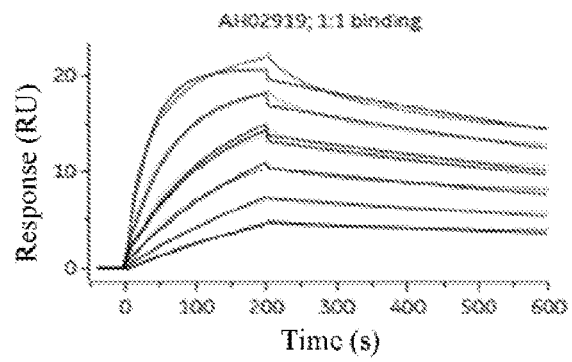
Figure 1C:
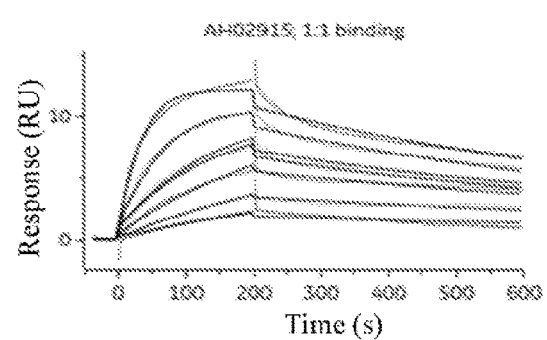
Figure 1D:
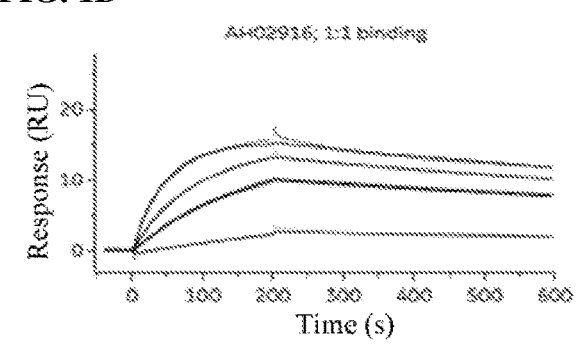
Figure 1E:
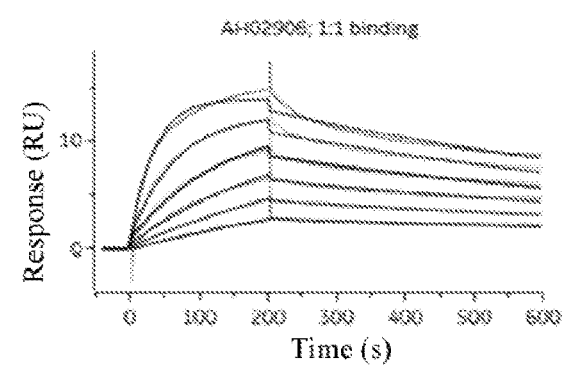
Figure 1F:
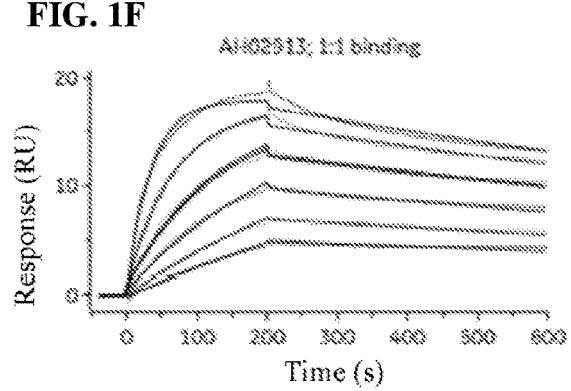
Figure 1G:
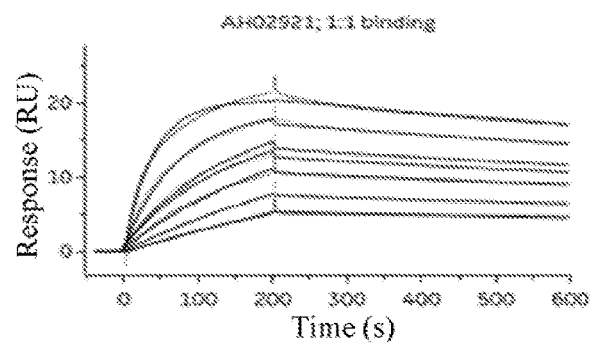
Figure 1H:
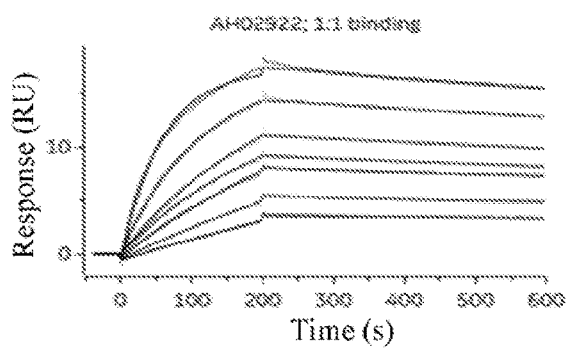
Figure 1I:
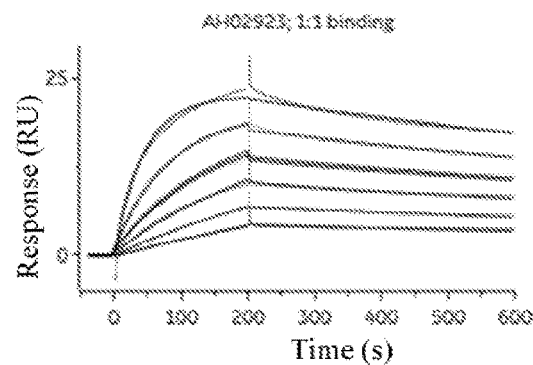
Figure 1J:
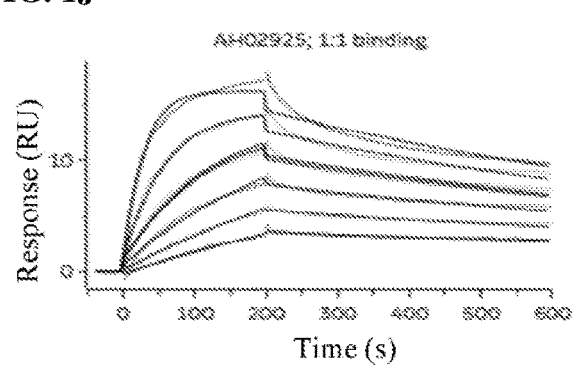
Figure 1K:
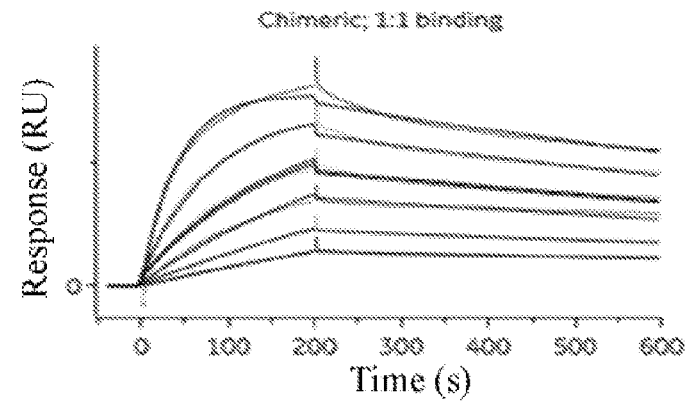
Figure 2A:
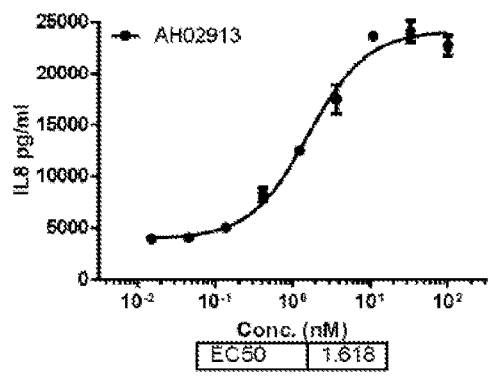
FIGS. 2A-2G show the detection of cell activity function in the presence of humanized anti-human OX40 monoclonal antibodies, including specifically: AH02913 (FIG. 2A), AH02916 (FIG. 2B), AH02919 (FIG. 2C), AH02921 (FIG. 2D), AH02923 (FIG. 2E), OX40 IgG (FIG. 2F); and OX40 ligand (FIG. 2G).
Figure 2B:
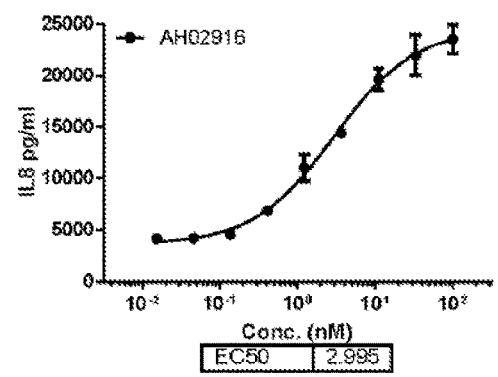
Figure 2C:
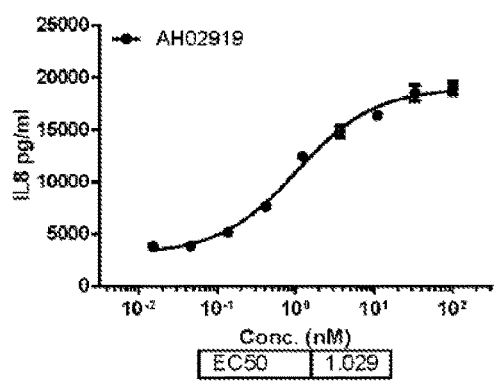
Figure 2D:
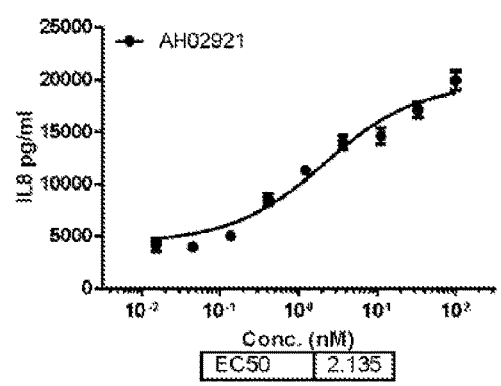
Figure 2E:
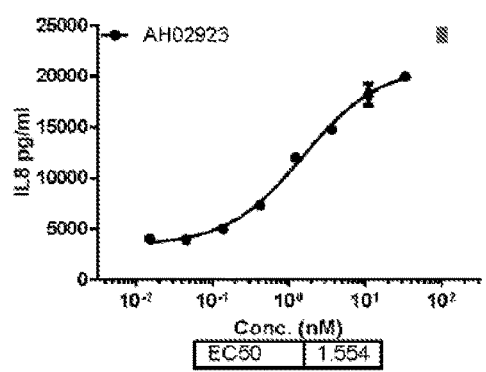
Figure 2F:
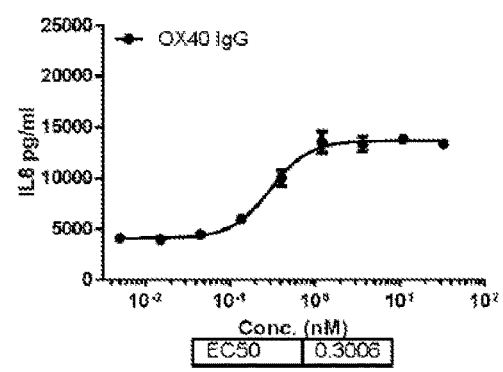
Figure 2G:
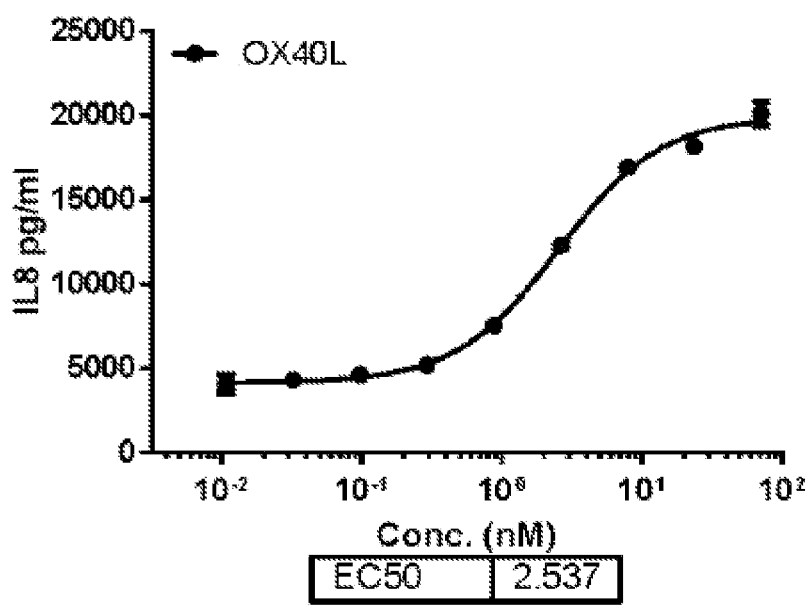

Unless otherwise specified, the technical and scientific terms used in the present invention have the meanings commonly understood by those skilled in the art to which the present invention belongs.

As used herein, the term "antibody" refers to an immunoglobulin molecule, which is usually a tetramer consisting of two identical heavy chains and two identical light chains connected to each other by disulfide bonds. According to conservative differences in amino acid sequences, the heavy chain and the light chain are divided into a variable region (V) at the amino terminal and a constant region (C) at the carboxy terminal. In the variable regions of the heavy chain and the light chain, there are three partial regions with a higher level of variations in the amino acid composition and arrangement order, which are the key positions for the antibody to bind to the antigen, and such region is also called a complementary determining region (CDR). Herein, the three heavy chain complementary determining regions are called HCDR1, HCDR2 and HCDR3, and the three light chain complementary determining regions are called LCDR1, LCDR2 and LCDR3 respectively. Both the variable regions of a heavy chain and the variable regions of a light chain compose an antigen binding site (Fv). According to amino acid sequences of the heavy chain constant regions, antibodies can be divided into different classes. There are five main types of intact antibodies: IgA, IgD, IgE, IgG and IgM, and some of these antibodies can be further divided into subclasses, for example, IgG1, IgG2, IgG3, IgG4, IgA1 and IgA2. The subunit structures and three-dimensional conformations of different classes of immunoglobulins are known in the art. The present invention is intended to include antibodies of any of the classes or subclasses.

As used herein, the term "antibody" is also intended to cover digested fragments or functional variants thereof, for example, antibody fragments capable of binding to OX40 or a part thereof, including but not limited to Fab (such as antibodies obtained by papain digestion), F(ab')2 (such as antibodies obtained by pepsin digestion) and Fv or scFv (such as antibodies obtained by molecular biology techniques).

As used herein, the term "monoclonal antibody" refers to a uniform antibody that only targets a specific epitope. Compared with ordinary polyclonal antibody preparations which typically include different antibodies against different antigenic determinants (epitopes), each monoclonal antibody is directed against a single antigenic determinant on an antigen. The modifier "monoclonal" refers to the uniform characteristics of an antibody, and is not interpreted as an antibody that needs to be produced by any specific method. The monoclonal antibodies of the present invention are preferably produced by a DNA recombination method or obtained by a screening method described elsewhere herein.

As used herein, the term "isolated polynucleotide" refers to a polynucleotide that does not occur naturally in nature, including polynucleotides isolated from nature (including organisms) through biological techniques and artificially synthesized polynucleotides. The isolated polynucleotide may be genomic DNA, cDNA, mRNA or other synthetic RNA, or a combination thereof. Herein provided is a number of nucleotide sequences encoding the heavy chain variable region and the light chain variable region of a humanized anti-OX40 monoclonal antibody. It should be noted that those skilled in the art can design nucleotide sequences that are not completely identical to the nucleotide sequences provided above, but both encode the same amino acid sequence according to the amino acid sequences of the heavy chain variable region and the light chain variable region provided herein on the basis of codon degeneracy. These modified nucleotide sequences are also included in the scope of the present invention.

As used herein, the "modification" of an amino acid residue/position refers to a primary amino acid sequence change relative to an original amino acid sequence, wherein the change comes from a change in the sequence involving an amino acid residue/position. For example, typical modifications include substituting (such as conservative or non-conservative substitution) a residue (at the position) with another amino acid, inserting one or more (generally less than 5 or 3) amino acids into a position adjacent to the residue/position and deleting the residue/position. "Amino acid substitution" or a change thereof refers to substitution of an existing amino acid residue with different amino acid residues in a predetermined (original) amino acid sequence. Relative to a polypeptide containing an original (or "wild-type") amino acid sequence, the modification generally preferably produces at least one physiological and biochemical activity change of a variant polypeptide. For example, for antibodies, the changed physiological and biochemical activity may be the binding affinity, binding capacity and/or binding effect for a target molecule.

The "percent (%) amino acid sequence identity" of a peptide or polypeptide sequence is defined as the percentage of amino acid residues in a candidate sequence identical to the amino acid residues in a specific peptide or polypeptide sequence after the sequences are compared and gaps are introduced when necessary to obtain the maximum percent sequence identity without considering any conservative substitutions as part of the sequence identity. Sequence comparison can be performed in a variety of ways within the skill of the art to determine the percentage of amino acid sequence identity, for example, publicly available computer software such as BLAST, BLAST-2, ALIGN or Megalign (DNASTAR) software is used. Those skilled in the art can determine appropriate parameters for measuring the comparison, including any algorithm required to obtain the maximum comparison over the entire length of the sequences being compared.

When referring to polynucleotide, the term "vector" as used herein refers to any molecule (such as nucleic acid, plasmid or virus) used to transfer nucleotide coding information into a host cell. The term "expression vector" or "expression cassette" refers to a vector suitable for expressing a target gene (nucleotide sequence to be expressed) in a host cell, and usually includes a target gene, a promoter, a terminator, a marker gene and other parts.

The term "host cell" as used herein refers to a cell that has been or is capable of being transformed with a nucleic acid sequence and thereby expressing a selected target gene. The term includes the offspring of a parent cell, that just need the selected target gene, regardless of whether the offspring and the original parent cell are the same in morphology or genetic composition. Commonly used host cells include bacteria, yeast, mammalian cells and the like.

The term "transformation" as used herein refers to the uptake of foreign or exogenous DNA by cells, and this technique can be used to introduce one or more foreign DNA portions into a suitable host cell. Physical and chemical methods (such as calcium chloride treatment) can be used to induce cells to stay in a physiological state that is optimal for ingesting and accommodating foreign DNA, that is, "competence".

When referring to a pharmaceutical composition, the term "effective amount" as used herein refers to an amount that can produce function or activity on humans and/or animals and can be accepted by humans and/or animals. "Pharmaceutically acceptable carrier" refers to a carrier for administration, including various excipients, diluents, buffers and the like. These substances are suitable for administration to humans and/or animals without excessive side effects, and at the same time, the substances are suitable for maintaining the vitality of the drugs or active agents therein.

Some aspects of the present invention will be described in detail below in conjunction with specific examples. Unless otherwise specified, the methods and materials in the examples described below are commercially available and conventional products.

EXAMPLES

Example 1: Humanization of Murine Anti-Human OX40 Antibody

1) A polynucleotide sequence was isolated from hybridoma cells, and sequenced to obtain the murine anti-human OX40 antibody 99A2A8D4E8 sequence (where the CDR regions were underlined (see, for example, SEQ ID NOs: 1-2) or italicized (see SEQ ID NOs: 5 and 6)).

99A2A8D4E8-VH

SEQ ID NO: 1
QIQLVQSGPELKKPGETVKISCKASGYTFTDYSMHWVKQAPGKGLKWMG

WISTETGEPTYADDFKGRFAFSLETSASTAYLQIKNLKNEDTASYFCAR

VRPWYLAVWGAGTTVTSS,

99A2A8D4E8-VL

SEQ ID NO: 2
DIQMTQTTSSLSASLGDRVTISC<u>RASQDISNYLN</u>WYQQKPDGTVKLLIY
<u>YTSRLYS</u>GVPSRFSGSGSGADYSLTVSNLEQEDIATYFC<u>QQANTLPLTF</u>
GAGTKLELK,

2) Construction of CDR-grafted plasmid of anti-human OX40 antibody

From the IMGT human V gene (F+ORF+in-frameP) database, the human Germline antibody sequence with the highest homology was selected as the receiving vector for humanization based on the alignment. The three heavy chain complementarity determining regions HCDR1, HCDR2 and HCDR3 and the three light chain complementarity determining regions LCDR1, LCDR2 and LCDR3 in the murine antibody were transferred to corresponding positions respectively, and the sites of post-translational modification (PTM) were analyzed. The result is shown in Table 1. Sequence analysis shows that the three sites M34, W50, and W102 are hot sites for post-translational modification (see, for example, SEQ ID NO: 3-4).

99A2A8D4E8-VH-GRAFTED

SEQ ID NO: 3
QVQLVQSGAEVKKPGASVKVSCKASGYTFT<u>DYSMH</u>WVRQAPGQRLEWMG
<u>WISTETGEPTYADDFKG</u>RVTITRDTSASTAYMELSSLRSEDTAVYYCAR
<u>VRPWYLAV</u>WGQGTLVTVSS,

99A2A8D4E8-VL-GRAFTED

SEQ ID NO: 4
DIQMTQSPSSLSASVGDRVTITC<u>RASQDISNYLN</u>WYQQKPGKAPKLLIY
<u>YTSRLYS</u>GVPSRFSGSGSGTDFTFTISSLQPEDIATYYC<u>QQANTLPLTF</u>
GGGTKLEIK,

TABLE 1

Risk analysis of sites of post-translational modification

| | 99A2A8D4E8 | |
| --- | --- | --- |
| | VH | VL |
| Homology to human germline (%) | 74.5% IGHV7-4-1*01 | 72.6% IGKV1-33*01 |
| Additional cysteine | No | No |
| N-glycosylation | No | No |
| Asparagine Deamidation | No | No |
| Aspartate isomerization | No | No |
| Oxidation | M34, W50, W102 | No |
| Hydrolysis | No | No |

3) The phage library CBM (bold font) was designed, the Phage-Fab and FASEBA-Fab plasmids of the anti-human OX40 antibody 99A2A8D4E8 VH-VL were constructed, and the back mutation sites in the humanized antibody were screened (see, for example, SEQ ID NOs: 5-6).

99A2A8D4E8_CBM

99A2A8D4E8-VH-CBM

SEQ ID NO: 5
QVQLVQSGPEVKKPGASVKISCKASGYTFT*DYSMH*WVKQAPGQGLEWMG
*WISTETGEPTYADDFKG*RFTFTLDTSASTAYLEISSLRSEDTAVYFCAR
*VRPWYLAV*WGQGTLVTVSS,

99A2A8D4E8-VL-CBM

SEQ ID NO: 6
DIQMTQSPSSLSASVGDRVTITC*RASQDISNYLN*WYQQKPGKAVKLLIY
*YTSRLYS*GVPSRFSGSGSGTDYTLTVSSLQPEDIATYFC*QQANTLPLTF*
GGGTKLEIK,

4) The affinity of the prokaryotically expressed antibody products and their VH/VL sequences (Table 2) was ranked, and the anti-human OX40 antibody sequence with the highest affinity was used for expression in a eukaryotic system.

TABLE 2

Screening of back mutations in humanized monoclonal antibodies, and ranking of antibodies with the highest affinity

| Ligand | Analyte | Back mutations (heavy chain + light chain) | ka (1/Ms) | kd (1/s) | KD (M) | Rmax (RU) | Kinetics Chi$^2$ (RU$^2$) | Kinetic model |
| --- | --- | --- | --- | --- | --- | --- | --- | --- |
| AH02906 | OX40-His | 4 + 3 | 3.28E+05 | 5.11E−03 | 1.56E−08 | 56 | 1.35E+00 | 1:1 binding |
| AH02913 | | 5 + 3 | 3.39E+05 | 4.25E−03 | 1.25E−08 | 41.1 | 1.36E−01 | 1:1 binding |
| AH02915 | | 5 + 2 | 2.15E+05 | 3.07E−03 | 1.43E−08 | 77 | 2.70E+00 | 1:1 binding |
| AH02916 | | 3 + 3 | 2.45E+05 | 3.84E−03 | 1.57E−08 | 48.5 | 1.35E−01 | 1:1 binding |
| AH02917 | | 5 + 2 | 2.88E+05 | 3.96E−03 | 1.37E−08 | 28.2 | 4.92E−01 | 1:1 binding |
| AH02919 | | 5 + 3 | 3.35E+05 | 5.05E−03 | 1.51E−08 | 110.9 | 1.16E+00 | 1:1 binding |
| AH02921 | | 8 + 3 | 3.88E+05 | 1.30E−03 | 3.35E−09 | 134.4 | 1.55E+00 | 1:1 binding |
| AH02922 | | 2 + 2 | 2.25E+05 | 5.34E−04 | 2.37E−09 | 53.2 | 5.55E−02 | 1:1 binding |
| AH02923 | | 5 + 2 | 3.17E+05 | 3.44E−03 | 1.08E−08 | 81.7 | 5.25E−01 | 1:1 binding |
| AH02925 | | 5 + 2 | 2.95E+05 | 4.39E−03 | 1.49E−08 | 77 | 3.05E+00 | 1:1 binding |

TABLE 2-continued

Screening of back mutations in humanized monoclonal antibodies, and ranking of antibodies with the highest affinity

| Ligand | Analyte | Back mutations (heavy chain + light chain) | ka (1/Ms) | kd (1/s) | KD (M) | Rmax (RU) | Kinetics Chi$^2$ (RU$^2$) | Kinetic model |
|---|---|---|---|---|---|---|---|---|
| Chimeric antibody | | 0 + 0 | 4.34E+05 | 4.87E-03 | 1.12E-08 | 29.7 | 1.43E-01 | 1:1 binding |

10 antibody sequences showing the highest affinity (see, for example, SEQ ID NO: 7-26):

AH02906-VH
SEQ ID NO: 7
QVQLVQSGAEVKKPGASVKVSCKASGYTFTDYSMHWVKQAPGQGLEWMGW
ISTETGEPTYADDFKGRFTITLDTSASTAYMELSSLRSEDTAVYYCARVR
PWYLAVWGQGTLVTVSS,

AH02913-VH
SEQ ID NO: 8
QVQLVQSGPEVKKPGASVKVSCKASGYTFTDYSMHWVKQAPGQGLEWMGW
ISTETGEPTYADDFKGRVTITLDTSASTAYMELSSLRSEDTAVYFCARVR
PWYLAVWGQGTLVTVSS,

AH02915-VH
SEQ ID NO: 9
QVQLVQSGAEVKKPGASVKVSCKASGYTFTDYSMHWVKQAPGQGLEWMGW
ISTETGEPTYADDFKGRVTITLDTSASTAYLEISSLRSEDTAVYYCARVR
PWYLAVWGQGTLVTVSS,

AH02916-VH
SEQ ID NO: 10
QVQLVQSGAEVKKPGASVKVSCKASGYTFTDYSMHWVKQAPGQGLEWMGW
ISTETGEPTYADDFKGRVTITLDTSASTAYMELSSLRSEDTAVYYCARVR
PWYLAVWGQGTLVTVSS,

AH02917-VH
SEQ ID NO: 11
QVQLVQSGAEVKKPGASVKVSCKASGYTFTDYSMHWVKQAPGQGLEWMGW
ISTETGEPTYADDFKGRFTITLDTSASTAYMELSSLRSEDTAVYFCARVR
PWYLAVWGQGTLVTVSS,

AH02919-VH
SEQ ID NO: 12
QVQLVQSGAEVKKPGASVKVSCKASGYTFTDYSMHWVKQAPGQGLEWMGW
ISTETGEPTYADDFKGRVTITRDTSASTAYLEISSLRSEDTAVYFCARVR
PWYLAVWGQGTLVTVSS,

AH02921-VH
SEQ ID NO: 13
QVQLVQSGPEVKKPGASVKVSCKASGYTFTDYSMHWVRQAPGQGLEWMGW
ISTETGEPTYADDFKGRFTITLDTSASTAYLEISSLRSEDTAVYFCARVR
PWYLTVWGQGTLVTVSS,

AH02922-VH
SEQ ID NO: 14
QVQLVQSGAEVKKPGASVKISCKASGYTFTDYSMHWVRQAPGQRLEWMGW
ISTETGEPTYADDFKGRVTITRDTSASTAYMELSSLRSEDTAVYYCARVR
PWYLVVWGQGTLVTVSS,

AH02923-VH
SEQ ID NO: 15
QVQLVQSGAEVKKPGASVKVSCKASGYTFTDYSMHWVRQAPGQGLEWMGW
ISTETGEPTYADDFKGRFTFTLDTSASTAYLELSSLRSEDTAVYYCARVR
PWYLAVWGQGTLVTVSS,

AH02925-VH
SEQ ID NO: 16
QVQLVQSGAEVKKPGASVKVSCKASGYTFTDYSMHWVKQAPGQGLEWMGW
ISTETGEPTYADDFKGRVTITRDTSASTAYLEISSLRSEDTAVYFCARVR
PWYLAVWGQGTLVTVSS,

AH02906-VL
SEQ ID NO: 17
DIQMTQSPSSLSASVGDRVTITCRASQDISNYLNWYQQKPGKAPKLLIYY
TSRLYSGVPSRFSGSGSGTDYTLTISSLQPEDIATYFCQQANTLPLTFGG
GTKLEIK,

AH02913-VL
SEQ ID NO: 18
DIQMTQSPSSLSASVGDRVTITCRASQDISNYLNWYQQKPGKAVKLLIYY
TSRLYSGVPSRFSGSGSGTDYTFTISSLQPEDIATYFCQQANTLPLTFGG
GTKLEIK,

AH02915-VL
SEQ ID NO: 19
DIQMTQSPSSLSASVGDRVTITCRASQDISNYLNWYQQKPGKAPKLLIYY
TSRLYSGVPSRFSGSGSGTDFTLTISSLQPEDIATYFCQQANTLPLTFGG
GTKLEIK,

AH02916-VL
SEQ ID NO: 20
DIQMTQSPSSLSASVGDRVTITCRASQDISNYLNWYQQKPGKAVKLLIYY
TSRLYSGVPSRFSGSGSGTDYTFTISSLQPEDIATYFCQQANTLPLTFGG
GTKLEIK,

AH02917-VL
SEQ ID NO: 21
DIQMTQSPSSLSASVGDRVTITCRASQDISNYLNWYQQKPGKAVKLLIYY
TSRLYSGVPSRFSGSGSGTDFTLTISSLQPEDIATYYCQQANTLPLTFGG
GTKLEIK,

AH02919-VL
SEQ ID NO: 22
DIQMTQSPSSLSASVGDRVTITCRASQDISNYLNWYQQKPGKAVKLLIYY

TSRLYSGVPSRFSGSGSGTDYTLTISSLQPEDIATYYCQQANTLPLTFGG

GTKLEIK,

AH02921-VL
SEQ ID NO: 23
DIQMTQSPSSLSASVGDRVTITCRASQDISNYLNWYQQKPGKAPKLLIYY

TSRLYSGVPSRFSGSGSGTDYTLTISSLQPEDIATYFCQQANTLPLTFGG

GTKLEIK,

AH02922-VL
SEQ ID NO: 24
DIQMTQSPSSLSASVGDRVTITCRASQDISNYLNWYQQKPGKAPKLLIYY

TSRLYSGVPSRFSGSGSGTDYTLTISSLQPEDIATYYCQQANTLPLTFGG

GTKLEIK,

AH02923-VL
SEQ ID NO: 25
DIQMTQSPSSLSASVGDRVTITCRASQDISNYLNWYQQKPGKAVKLLIYY

TSRLYSGVPSRFSGSGSGTDYTFTISSLQPEDIATYYCQQANTLPLTFGG

GTKLEIK,

AH02925-VL
SEQ ID NO: 26
DIQMTQSPSSLSASVGDRVTITCRASQDISNYLNWYQQKPGKAVKLLIYY

TSRLYSGVPSRFSGSGSGTDFTLTISSLQPEDIATYYCQQANTLPLTFGG

GTKLEIK,

Example 2: Recombinant Production of Humanized Antibodies

The VH and VL sequences of the selected antibody were codon optimized, which linked a secretion signal peptide at the 5' end, then linked to the heavy chain constant region sequence of human antibody IgG1 and kappa light chain constant region sequence respectively. Then the products were respectively cloned into the pTT5 expression vector to prepare a human antibody DNA sequence in order to be expressed and secreted in mammalian cells. The plasmid was co-transfected with PEI into HEK293-6E cells cultured in suspension for transient expression. During transfection, the cell density was maintained at $1\times10^6$ cells/mL, and the ratio of PEI:DNA was 3:1. The cells were cultured in an incubator at 37° C. and 5% $CO_2$ with shaking at 105 rpm. After 24 hrs of transfection, 0.5% Trypton N-1 was added. After 5 days, the cell culture supernatant was collected for antibody purification. Before purification, the tubing and protein A column were depyrogenated with 0.2M NaOH. The column was re-equilibrated with a buffer containing 0.05M Tris and 1.5M NaCl (pH 8.0). Subsequently, the harvested cell culture supernatant was diluted 1:1 with 2× the above buffer and sterilized by filtration. The filtered supernatant was incubated with the protein A column at room temperature for 2 hrs. After washing the column with 1× the above buffer, IgG was eluted off with sterile 0.1M sodium citrate (pH 3.5). The eluate was collected and neutralized with one-ninth volume of sterile 1M Tris-HCl (pH 9). Under sterile conditions, the product buffer was changed to PBS (pH 7.4) to remove any elution buffer and the sample was concentrated. After concentration, the antibody was quantified by OD280 nm using an extinction coefficient Ec (0.1%) of 1.43.

The purified antibody was analyzed by SDS-PAGE using 10% precast gel (GenScript) in the BioRad electrophoresis system. The gel was stained with Estain 2.0 (GenScript) and the molecular weight and purity were estimated by comparing the stained band with Protein Ladder (GenScript) (Table 3).

TABLE 3

Recombinant production of humanized antibodies

| Sample | Transfection system (ml) | Antibody concentration (mg/ml) | Antibody volume (ml) | Total antibody amount (mg) | Antibody purity (%) |
|---|---|---|---|---|---|
| AH02906 | 50 | 1.12 | 3.00 | 3.35 | 96% |
| AH02913 | 100 | 0.22 | 6.50 | 1.43 | 93% |
| AH02915 | 50 | 1.56 | 2.60 | 4.07 | 90% |
| AH02916 | 100 | 0.16 | 6.50 | 1.02 | 93% |
| AH02917 | 50 | 0.54 | 2.70 | 1.46 | 94% |
| AH02919 | 50 | 0.64 | 2.80 | 1.80 | 91% |
| AH02921 | 50 | 1.22 | 2.70 | 3.28 | 90% |
| AH02922 | 50 | 0.93 | 2.50 | 2.33 | 93% |
| AH02923 | 100 | 0.24 | 6.50 | 1.59 | 93% |
| AH02925 | 50 | 0.59 | 2.80 | 1.66 | 95% |
| Chimeric antibody | 200 | 0.12 | 3.00 | 0.36 | 95% |

Example 3: Affinity Determination of Humanized Monoclonal Antibody

The chip surface was equilibrated with HBS-EP buffer at a flow rate of 10 μl/min for 5 min, and then a 1:1 mixture of "NHS+EDC" was injected at a flow rate of 10 μl/min for 100 sec to activate the chip. The antigen protein (OX40-HIS) diluted in 10 mM sodium acetate buffer was injected for about 180 sec at a flow rate of 10 μl/min for coupling, and finally ethanolamine was injected for 200 sec at a flow rate of 10 μl/min to block the surface.

Three pre-cycles were performed with the HBS-EP buffer as a sample to balance the chip to stabilize the baseline. A low concentration of antibody was injected at a flow rate of 30 μl/min for 200 sec, to allow the antigen to bind to the antibody, and then the buffer was injected at a flow rate of 30 μl/min for 400 sec for dissociation. 10 mM Gly-HCl pH2.0 was injected three times each for 30 sec at a flow rate of 30 μl/min for regeneration, to complete one cycle.

The antibody concentration was changed to carry out the cycle for measurement at a next gradient concentration until all gradient concentrations (2.5 nM, 5 nM, 10 nM, 20 nM, 40 nM, and 80 mM) and the replicate (such as 20 nM) were tested. The experimental data was double subtracted (minus the background values of the control channel and zero concentration), and fitted to the "1:1 binding" model in the Biacore 8K evaluation software. Biacore 8K was used to determine the affinity of the antibody to the OX40-HIS recombinant protein.

As shown in FIG. 1 and Table 4, the affinity of monoclonal antibodies to OX40-HIS (AH02913, AH02916, AH02919, AH02921, AH02922, and AH02923) specific to human OX40 is measured by Biacore to reach the nM level. These results indicate that the antibodies screened by the present invention have very high affinity.

TABLE 4

Affinity determination of humanized anti-human OX40-HIS monoclonal antibody

| Ligand | Analyte | $k_a$ (1/Ms) | Back mutations (heavy chain + light chain) | $k_d$ (1/s) | $K_D$ (M) | Rmax (RU) | Kinetics Chi$^2$ (RU$^2$) |
|---|---|---|---|---|---|---|---|
| OX40/His | AH02906 | 4.08E+05 | 4 + 3 | 1.16E−03 | 2.83E−09 | 13.4 | 8.18E−02 |
| | AH02913 | 3.81E+05 | 5 + 3 | 6.70E−04 | 1.76E−09 | 17.7 | 7.95E−02 |
| | AH02915 | 4.72E+05 | 5 + 2 | 1.42E−03 | 3.00E−09 | 11.2 | 6.77E−02 |
| | AH02916 | 2.68E+05 | 3 + 3 | 6.59E−04 | 2.46E−09 | 15.9 | 5.22E−02 |
| | AH02917 | 4.07E+05 | 5 + 2 | 1.06E−03 | 2.60E−09 | 13.8 | 7.76E−02 |
| | AH02919 | 3.72E+05 | 5 + 3 | 7.76E−04 | 2.09E−09 | 20.1 | 1.12E−01 |
| | AH02921 | 3.27E+05 | 8 + 3 | 4.39E−04 | 1.34E−09 | 20.8 | 7.71E−02 |
| | AH02922 | 2.13E+05 | 2 + 2 | 2.90E−04 | 1.36E−09 | 18.3 | 2.06E−02 |
| | AH02923 | 2.87E+05 | 5 + 2 | 6.16E−04 | 2.15E−09 | 22.9 | 9.64E−02 |
| | AH02925 | 5.20E+05 | 5 + 2 | 1.15E−03 | 2.22E−09 | 14.9 | 1.16E−01 |
| | Chimeric antibody | 3.39E+05 | 0 + 0 | 8.14E−04 | 2.40E−09 | 19.2 | 8.54E−02 |

Example 4: Verification of Cell Activity Function in the Presence of Humanized Anti-Human OX40 Monoclonal Antibody A functional cell line overexpressing OX40 was used to test the function of anti-OX40 monoclonal antibodies. The OX40 overexpressing functional cell line was coated on a 384 empty plate, and incubated overnight at 37° C. and 5% $CO_2$. Different concentrations of an antibody sample were added to each well, an antibody-free well was used as a background control, human IgG1 was as a negative control, and OX40L was used as a positive control for anti-OX40 monoclonal antibodies. After incubation for 24 hrs at 37° C. and 5% $CO_2$, 100 μl supernatant was taken from each well to detect IL-8 content (Cisbio's test kit). In the detection of OX40 agonistic antibodies, the OX40 agonistic antibodies directly act on the OX40 protein on the cell membrane to activate the cells to secrete IL-8. As more IL-8 is secreted, the activation of T cells increases.

Experimental results show that humanized anti-human OX40 monoclonal antibody (AH02913, AH02916, AH02919, AH02921, AH02923) can specifically activate the positive immune regulation by OX40 and activate T cells to secrete cytokines. The corresponding $EC_{50}$ is 1.62 nM, 3.00 nM, 1.03 nM, 2.14 M, and 1.55 nM respectively (FIG. 2 and Table 5).

TABLE 5

Cellular activation response of humanized anti-human OX40 monoclonal cells

| | Best-fit values | | | |
|---|---|---|---|---|
| Sample | Bottom | Top | LogEC$_{50}$ | HillSlope | EC$_{50}$ (nM) |
| OX40L | 4130 | 19947 | 0.4043 | 1.187 | 2.54 |
| OX40 IgG | 4092 | 13695 | −0.5221 | 1.89 | 0.30 |
| AH02913 | 3954 | 24152 | 0.2089 | 1.147 | 1.62 |
| AH02916 | 3591 | 24602 | 0.4765 | 0.8311 | 3.00 |
| AH02919 | 3063 | 18983 | 0.01225 | 0.8714 | 1.03 |
| AH02921 | 4417 | 19545 | 0.3293 | 0.7428 | 2.14 |
| AH02923 | 3353 | 20969 | 0.1913 | 0.8662 | 1.55 |

Example 5: Determination of Cross-Recognition Ability of Humanized Monoclonal Antibody Recombinant human OX-40 protein and recombinant monkey OX-40 protein were respectively used to detect the cross-recognition ability of humanized monoclonal antibodies for human/monkey OX-40 protein.

The ELISA plate (Nunc) was coated with 100 μl/well of 1 μg/ml recombinant OX40-His protein in PBS at 4° C. overnight. The plate was washed with PBS-T (0.05% Tween) and blocked with 200 μl/well of PBST containing 1% BSA at 37° C. for 0.5 hr. Then the blocking buffer was discarded, 100 μl of 1000 ng/ml purified antibody was added to the first well, 3-fold serial dilutions were made, and a total of 11 test concentration gradients were given. Then the system was incubated for 1 hr at room temperature. The plate was washed three times with PBST and incubated with 100 μl/well of horseradish peroxidase-conjugated goat anti-human Fab fragment-IgG (Fab-specific) (GenScript) at 37° C. for 0.5 hr. The plate was washed 5 times with PBST, and then a TMB developing solution (GenScript) was added and incubated at room temperature for 15 min in the dark. The reaction was terminated by adding 50 μl of 1 M HCl stop solution (Sigma). The plate was read at 450 nm on a microplate reader.

Figure 3A:
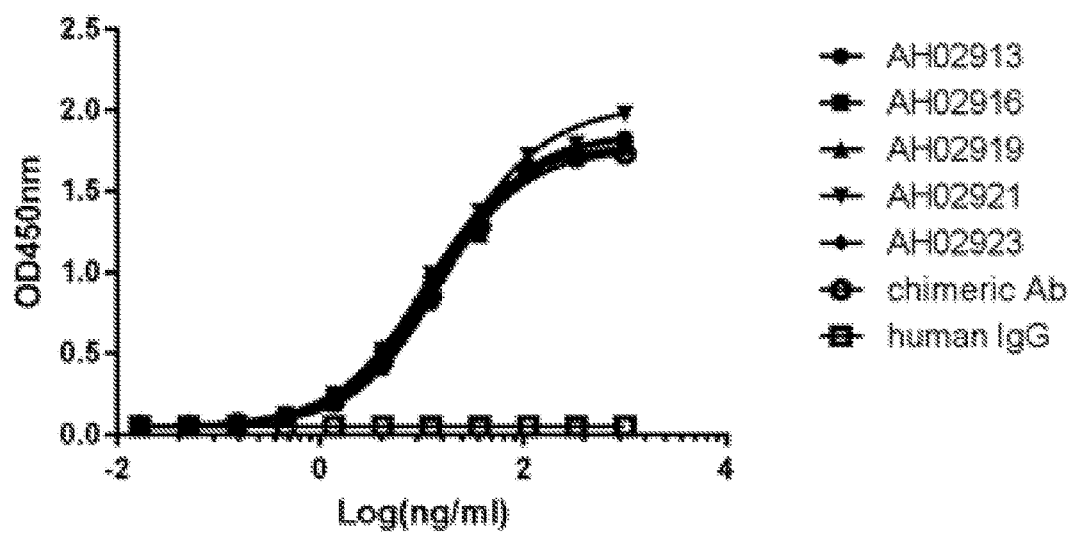
Figure 3B:
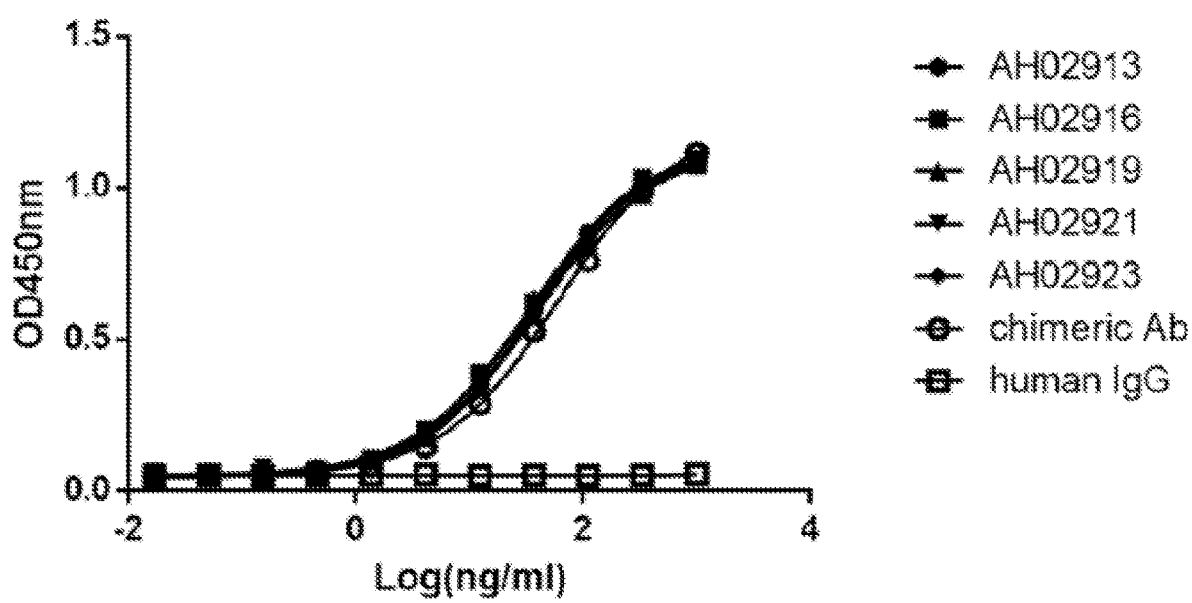
Figure 4A:
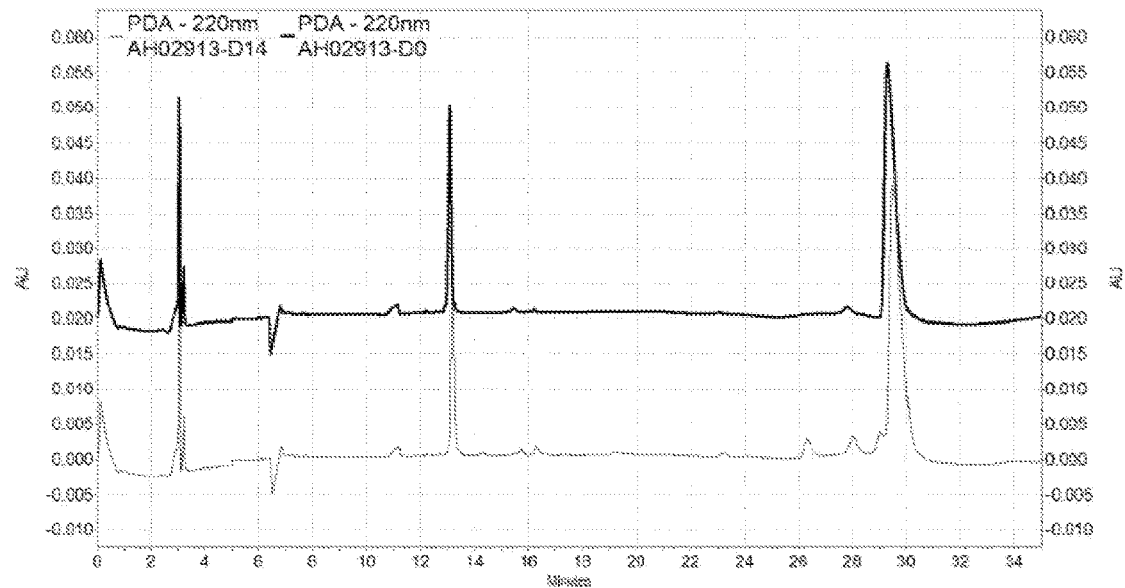
FIGS. 4A-4E show the thermal stability analysis of purified monoclonal antibodies, specifically the thermal stability analysis of humanized anti-human OX40 monoclonal antibodies utilizing SEC-HPLC (treated at 40° C. for 2 weeks), including AH02913-0/14 days-SEC-HPLC (FIG. 4A), AH02916-0/14 days-SEC-HPLC (FIG. 4B), AH02919-0/14 days-SEC-HPLC (FIG. 4C), AH02921-0/14 days-SEC-HPLC (FIG. 4D), and AH02923-0/14 days-SEC-HPLC (FIG. 4E)
Figure 4B:
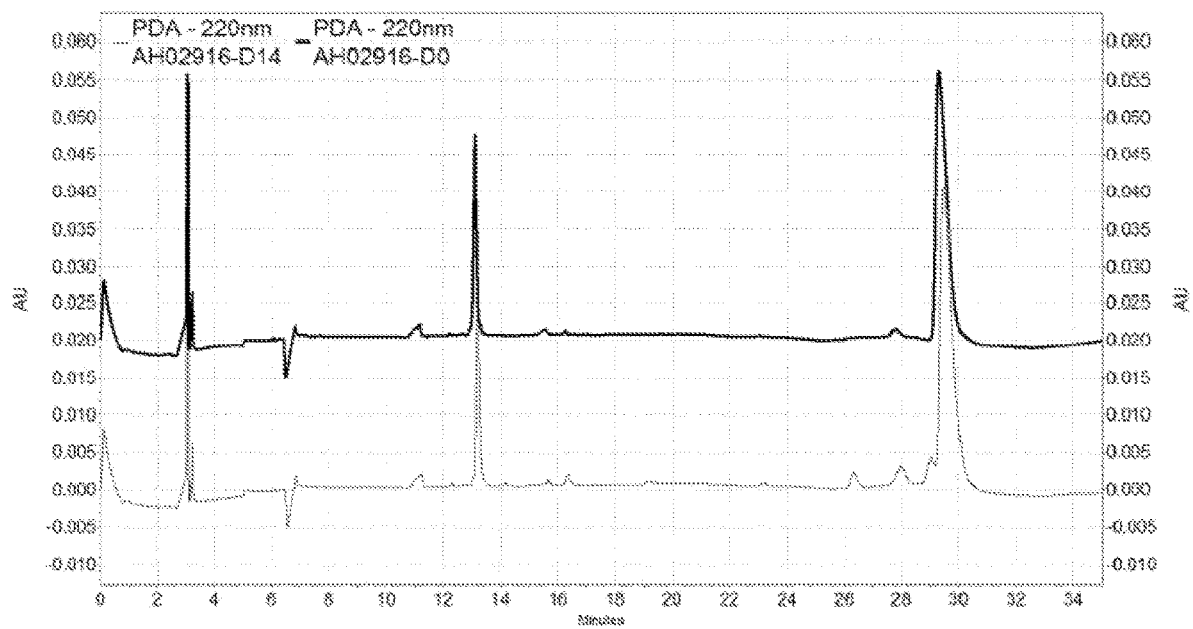
Figure 4C:
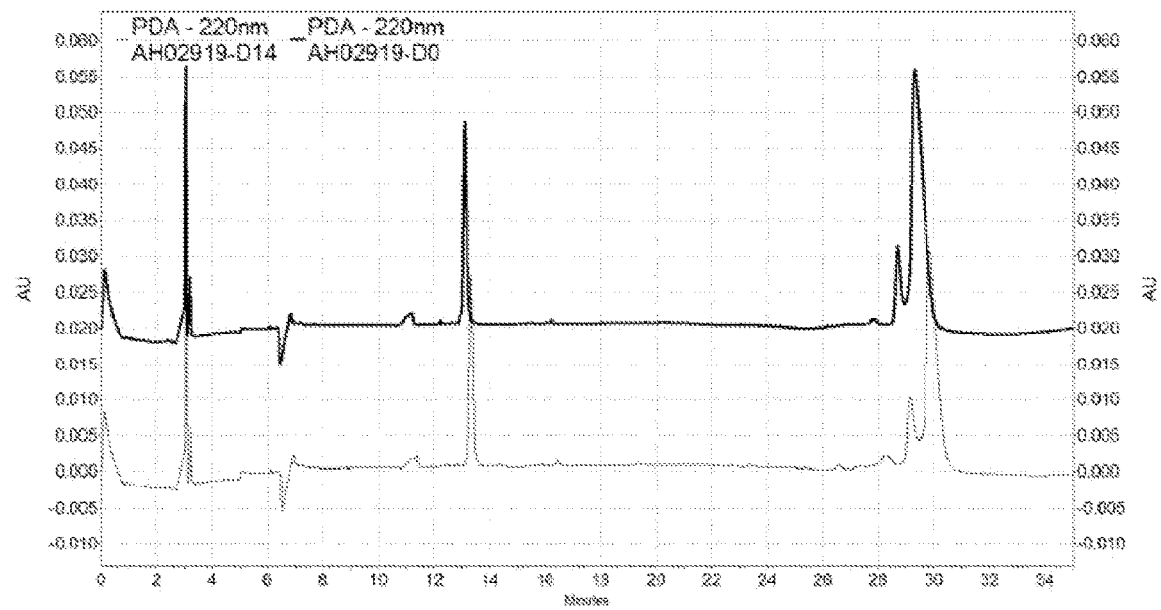
Figure 4D:
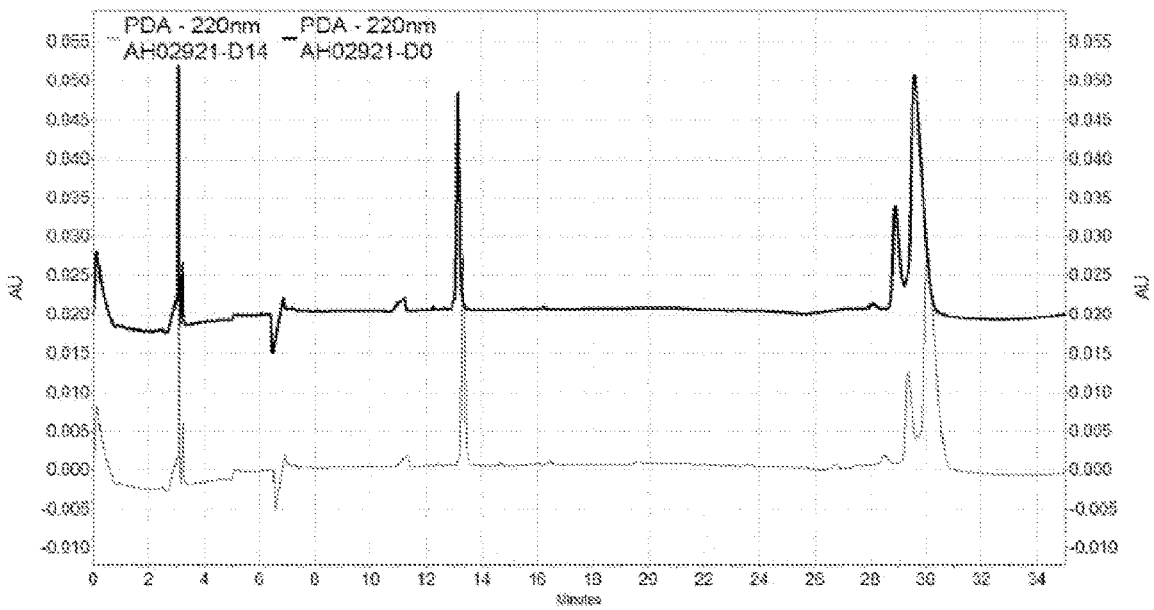
Figure 4E:
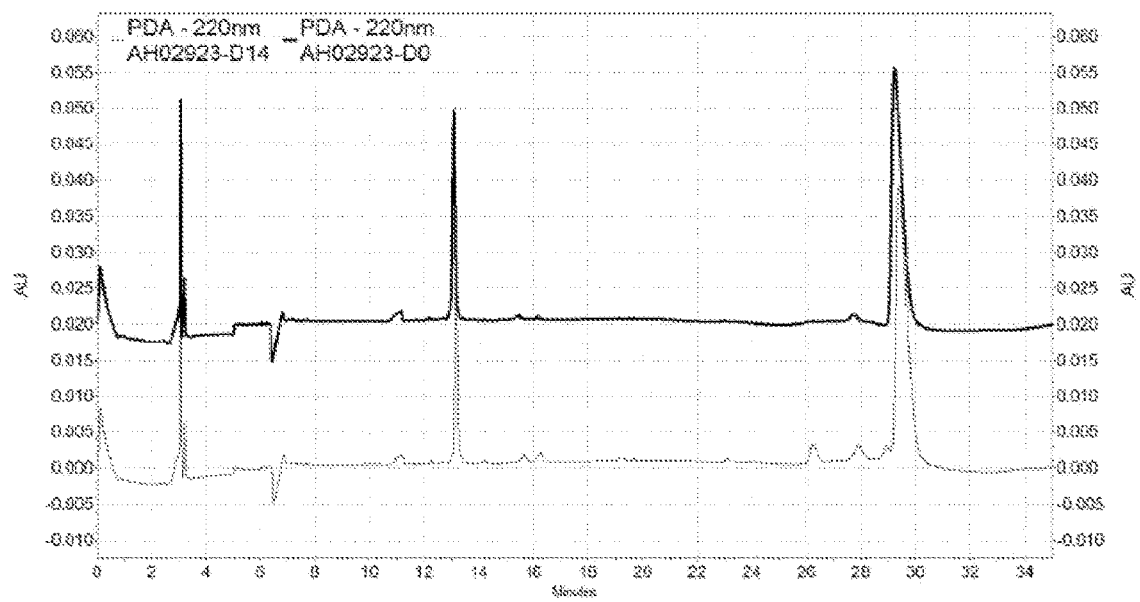
Figure 5A:
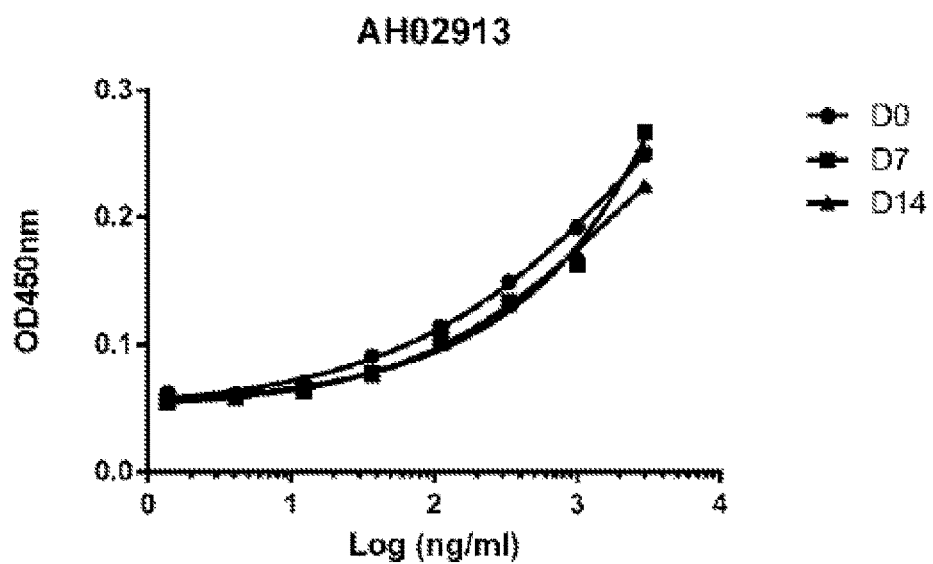
FIGS. 5A-5E show the thermal stability analysis of purified monoclonal antibodies, specifically thermal stability analysis by ELISA of humanized anti-human OX40 monoclonal antibodies (treated at 40° C. for 2 weeks), including AH02913 (FIG. 5A), AH02916 (FIG. 5B), AH02919 (FIG. 5C), AH02921 (FIG. 5D) and AH02923 (FIG. 5E)
Figure 5B:
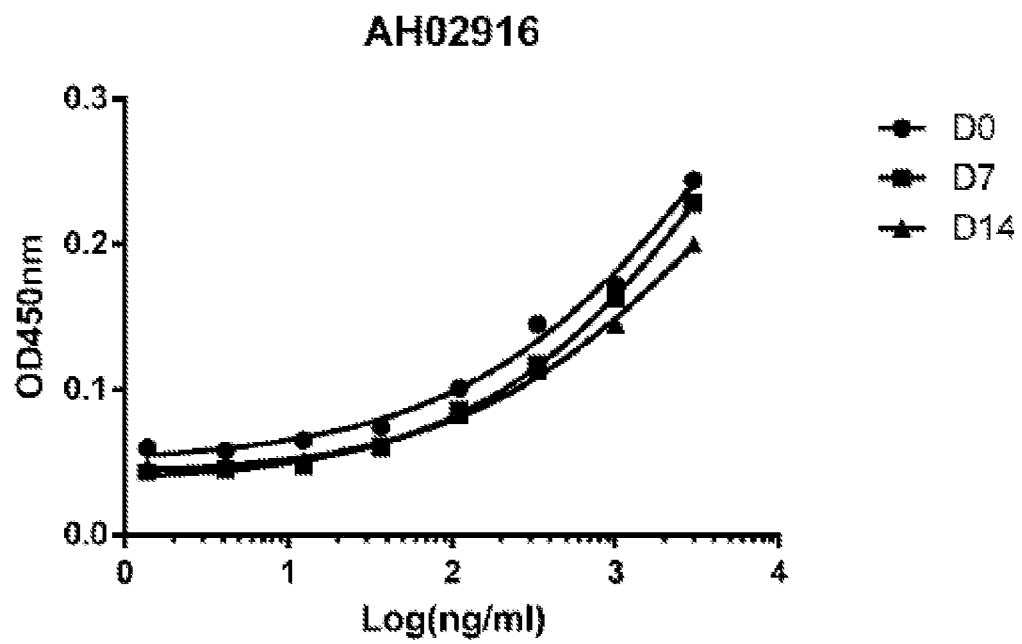
Figure 5C:
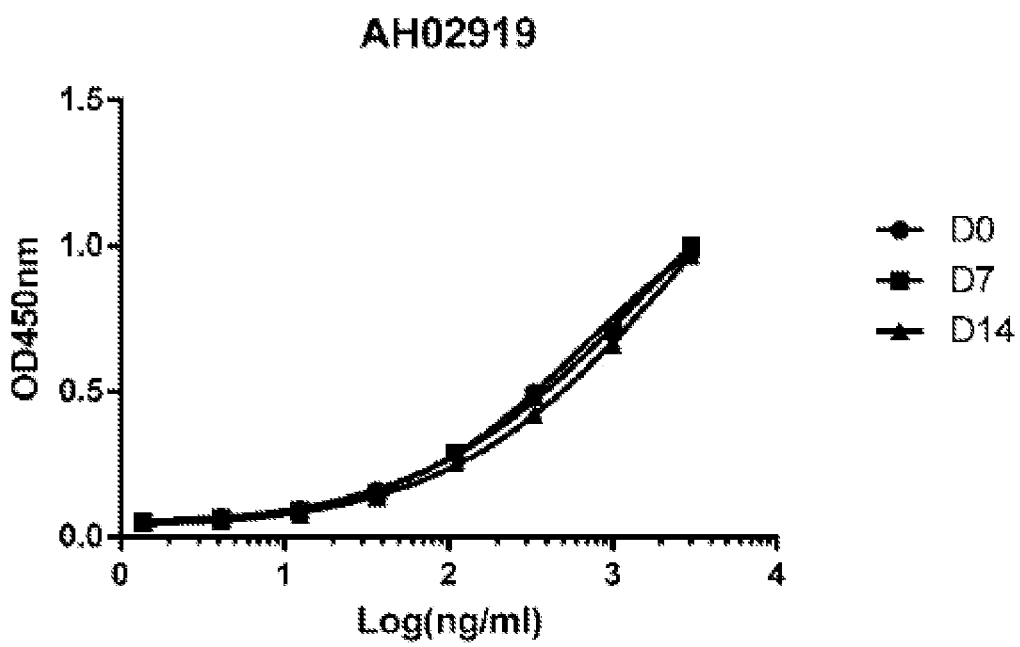
Figure 5D:
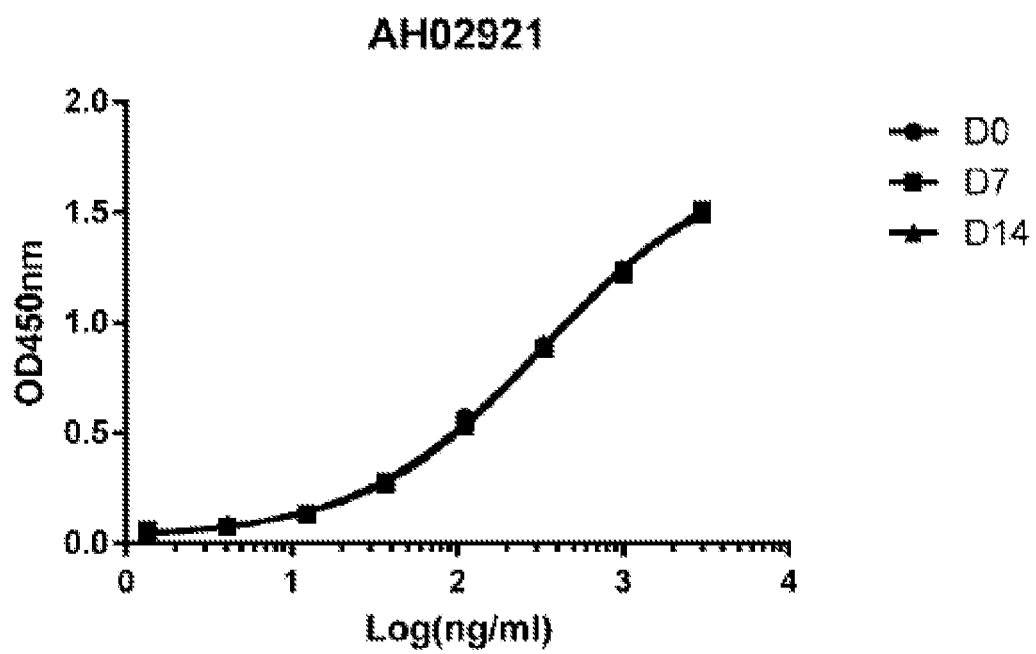
Figure 5E:
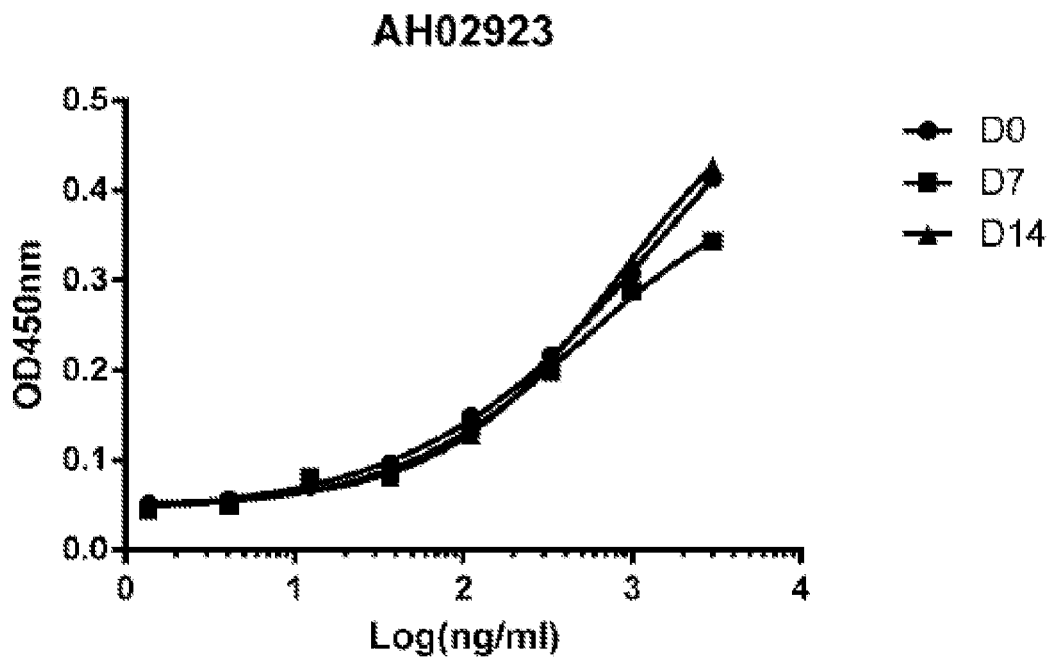
Figure 6A:
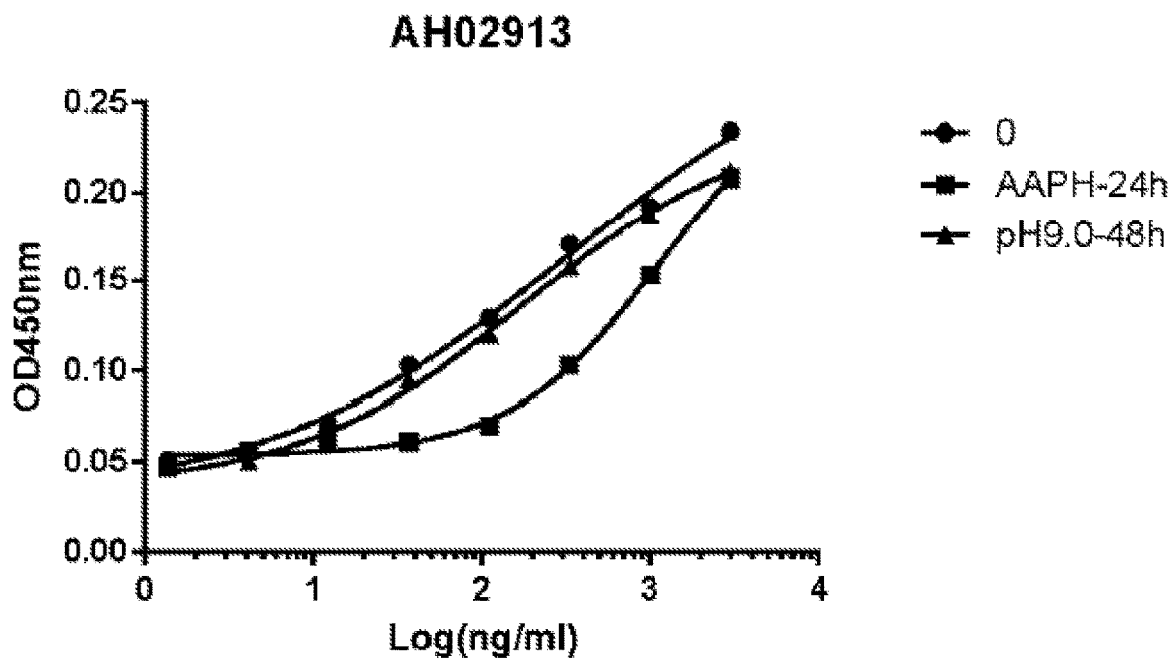
FIGS. 6A-6E show the detection and analysis of the pharmaceutical potential of purified monoclonal antibodies, specifically ELISA analysis of humanized anti-human OX40 monoclonal antibodies after oxidative stress/deamidation stress test, including AH02913 (FIG. 6A), AH02916 (FIG. 6B), AH02919 (FIG. 6C), AH02921 (FIG. 6D) and AH02923 (FIG. 6E).
Figure 6B:
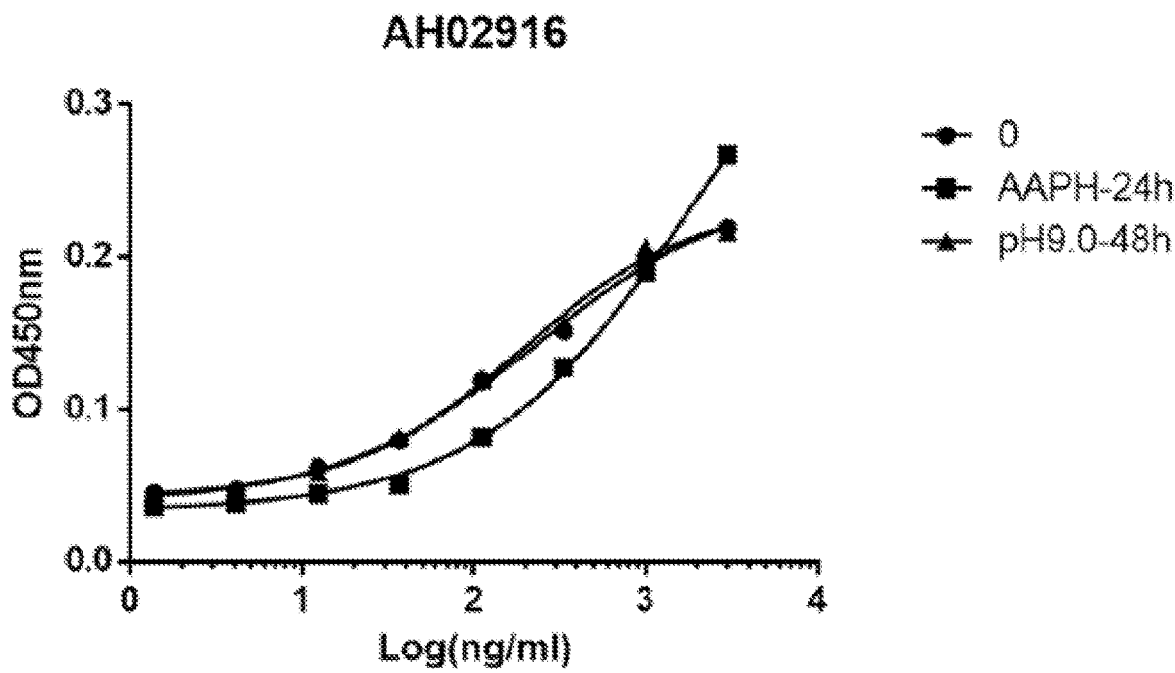
Figure 6C:
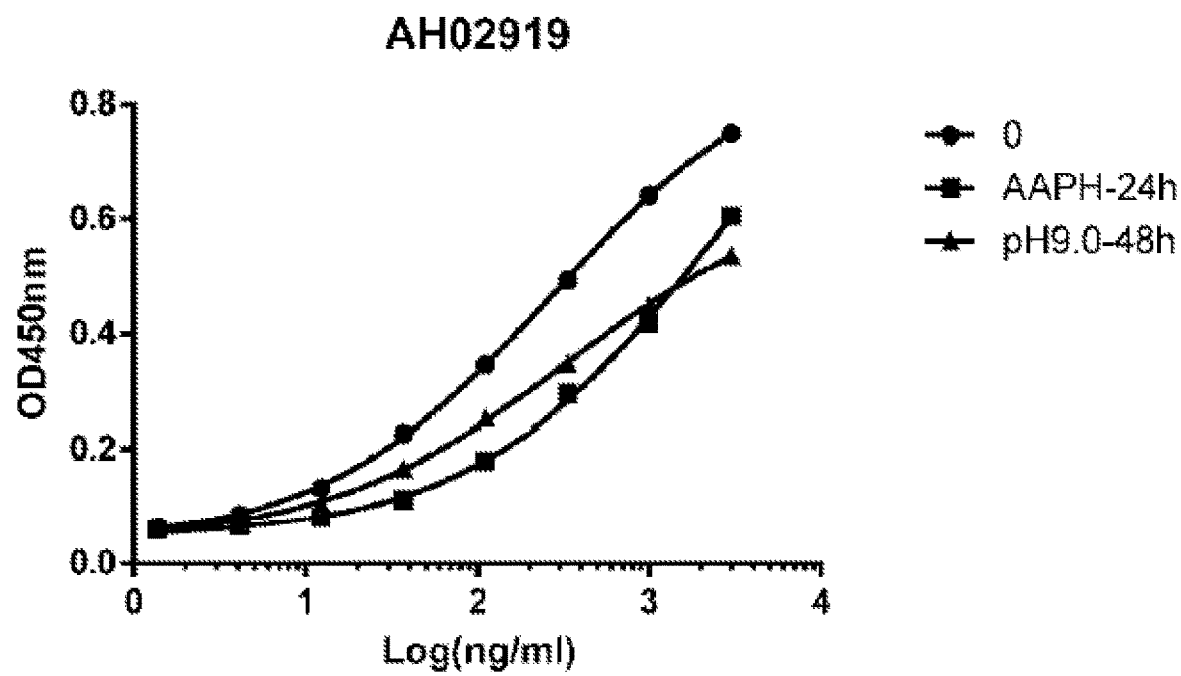
Figure 6D:
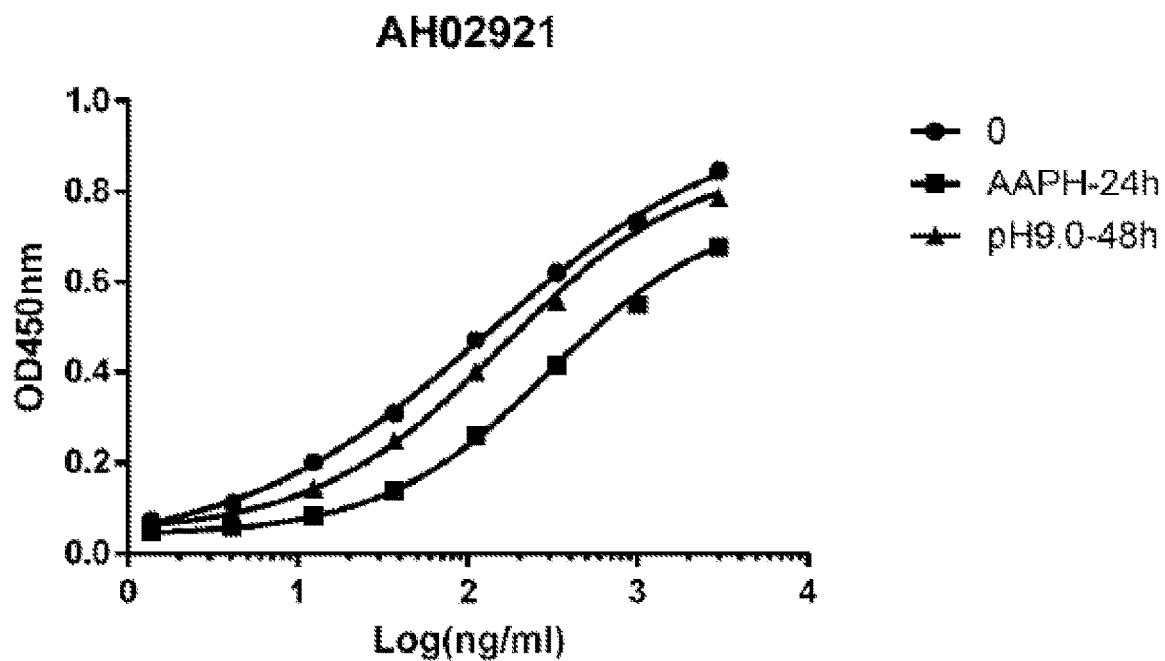
Figure 6E:
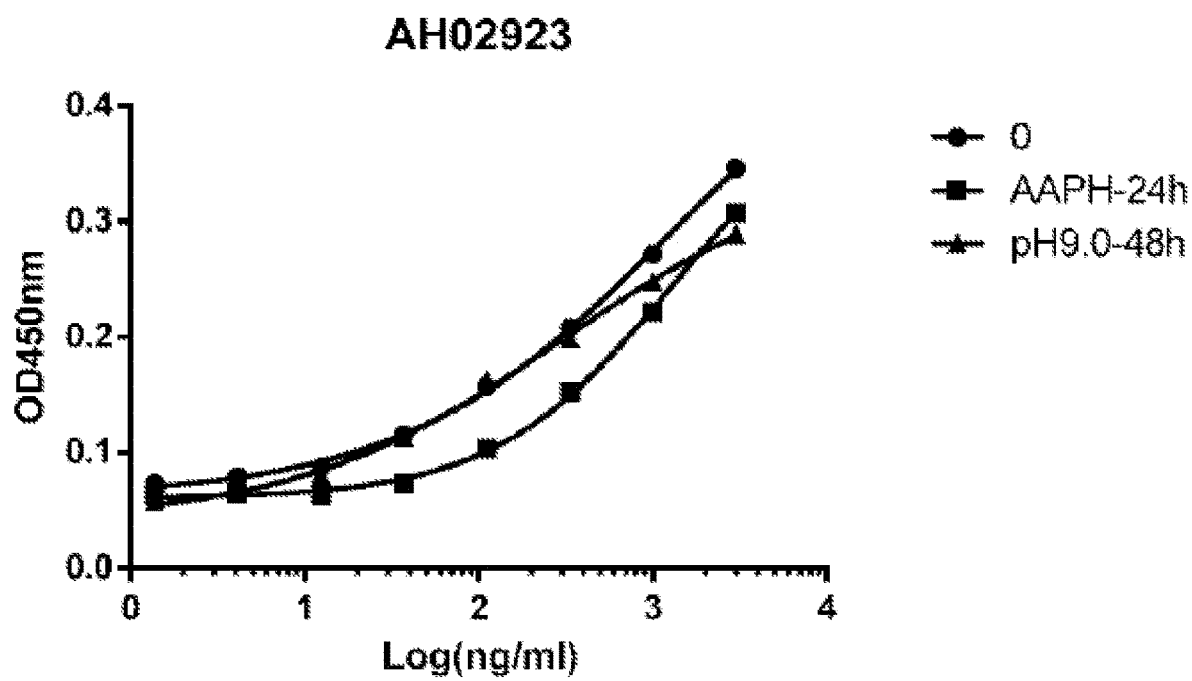

The results show that the recombinantly expressed antibodies can jointly recognize both human OX-40 protein and recombinant monkey OX-40 protein (FIG. 3 and Table 6). FIG. 3A shows the interaction between each monoclonal antibody and human OX-40 protein utilizing an ELISA assay; and FIG. 3B shows the interaction between each monoclonal antibody and monkey OX-40 protein utilizing an ELISA assay.

TABLE 6

$EC_{50}$ detected by ELISA of each recombinant antibody recognizing human OX-40 protein and monkey OX-40 protein

| AH02913 | AH02916 | AH02919 | AH02921 | AH02923 | Chimeric antibody |
|---|---|---|---|---|---|
| $EC_{50}$ (ng/ml) detected by ELISA of each recombinant antibody recognizing human OX-40 protein | | | | | |
| 16.09 | 13.09 | 14.32 | 16.1 | 10.73 | 13.84 |
| $EC_{50}$ (ng/ml) detected by ELISA of each recombinant antibody recognizing monkey OX-40 protein | | | | | |
| 35.28 | 32.29 | 39.15 | 37.63 | 30.28 | 61.77 |

Example 6: Evaluation of the Pharmaceutical Potential of Humanized Anti-Human OX40 Monoclonal Antibody AH02913, AH02916, AH02919, AH02921, AH02923 and chimeric antibody were respectively expressed in a 200 ml system to obtain a purified antibody sample of more than 5 mg and having an endotoxin content controlled at the level of 3 EU/mg for subsequent experiments.

1. Thermal Stability Test 1.1. Differential Scanning Fluorimetry to Detect the Denaturation Temperature Tm of the Sample

TABLE 7

Detection of Tm of humanized anti-human OX40 monoclonal antibody

| Sample | Concentration (mg/ml) | Tm Onset | Tagg | Tm |
|---|---|---|---|---|
| AH02913 | 0.11 | 64.7° C. | 74.3° C. | 71.0° C. |
| AH02916 | 1.39 | 54.4° C. | 72.7° C. | 62.9° C. |
| AH02919 | 0.64 | 58.2° C. | 75.8° C. | 77.2° C. |
| AH02921 | 1.21 | 63.9° C. | 74.2° C. | 72.0° C. |
| AH02923 | 0.23 | 59.7° C. | 79.1° C. | 70.5° C. |
| Chimeric antibody | 0.12 | 55.9° C. | 76.1° C. | 70.1° C. |

The test results show (Table 7) that the Tm of AH02913, AH02919, AH02921, and AH02923 are all above 70° C., and only the Tm of AH02916 is 62.9° C.

1.2. Experimental Settings for Thermal Stability Test

A. The durability test was conducted with an antibody sample concentration of >5 mg/ml.

The antibody samples were treated separately at 40° C., and then centrifuged to remove the pellet. Then the amount of remaining antibody was evaluated by ELISA. (test after treatment at 40° C. for 7 days and 14 days separately; for each test, the untreated sample stored at −80° C. is used as a control)

The treated sample was subjected to SEC-HPLC and nr-SDS test.

The results are shown in FIG. 4 and Table 8. The thermally treated AH02913, AH02916, AH02919, AH02921 and AH02923 antibody samples do not have a large amount of aggregate, and have stable antibody purity.

TABLE 8

Purity detection by nr-SDS of humanized anti-human OX40 monoclonal antibody before and after heat treatment

| Sample | Before antibody peak (%) | Antibody peak (%) |
|---|---|---|
| AH02913-D0 | 3.99 | 96.01 |
| AH02913-D14 | 17.87 | 82.13 |
| AH02916-D0 | 4.6 | 95.4 |
| AH02916-D14 | 16.03 | 83.97 |
| AH02919-D0 | 16.51 | 83.49 |
| AH02919-D14 | 24.9 | 75.1 |
| AH02921-D0 | 21.87 | 78.12 |
| AH02921-D14 | 27.57 | 72.44 |
| AH02923-D0 | 4.27 | 95.73 |
| AH02923-D14 | 17.55 | 82.45 |

In addition, the ELISA test (FIG. 5) of the humanized anti-human OX40 monoclonal antibodies after the thermal stability stress test show that the thermally treated AH02913, AH02916, AH02919, AH02921 and AH02923 antibody samples are not affected in their ability to recognize the human OX-40 protein.

2. Pharmaceutical Potential Test

The sequence analysis (Table 1) of the CDR region of the anti-human OX40 monoclonal antibodies shows that the VH region is predicted to have hot sites of oxidative modification at positions M34, W50, and W102 of the heavy chain variable region. The humanized anti-human OX40 monoclonal antibodies were subjected to the following tests separately.

A. Oxidative stress test: The antibody molecules were transferred to a 20 mM ammonium acetate solution (pH 5.0), added with AAPH (2,2'-azobis(2-amidinopropane)) (50:1) and treated at 40° C. for 24 hrs in the dark.

B. Deamidation stress test: The antibody molecules were placed in a PBS solution (pH 9) at 40° C. for 48 hrs.

The effect of oxidative modification/deamidation modification on the antigen recognizing ability of the antibody molecules was determined.

The treated antibody samples were detected by MS to determine the proportion of a corresponding chemical change in the amino acid molecules, and to determine the degree of aggregate of the antibody molecules by SEC-HPLC.

The results show (Table 9-10) that the coverage rate of MS detection reaches about 95%, and reliable results are obtained. No oxidative modification is detected at M34 and W50 in the antibody molecules before and after each treatment; no oxidative modification is detected at W102 before treatment, and 31.43% of oxidative modification is detected at W102 in the AH02913 sample after AAPH-24 treatment; 54.33% of oxidative modification is detected at W102 in the AH02916 sample after AAPH-24 treatment; and 35.78% of oxidative modification is detected at W102 in the AH02923 sample after AAPH-24 treatment. It is also detected that M428 and M252 also undergo oxidative modification in the constant region. Therefore, there is a potential of oxidative modification at the W102 position in the CDR sequences of AH02913, AH02916 and AH02923.

Moreover, the MS analysis after the deamidation stress test shows that no deamidation modification occurs in the CDR sequences of AH02913, AH02916 and AH02923, which is consistent with the result of sequence analysis.

The verification results by ELISA (FIG. 6) show that AH02913, AH02916, AH02919, AH02921 and AH02923 antibody molecules still retain good antigen binding ability under the conditions of oxidative stress treatment and deamidation treatment.

TABLE 9

Pharmaceutical potential detection and analysis: MS detection of humanized anti-human OX40 monoclonal antibodies after oxidative stress test

| Sample name | Peptide fragment | Sequence | Modification | Modification percentage | XIC area |
|---|---|---|---|---|---|
| AH02913-AAPH-24h | C1-2 | DIQMTQSPSSL (SEQ ID NO: 33) | Oxidative @4(4) | 8.55% | 8.24E+05 |
| AH02913-AAPH-24h | C1-2 | DIQMTQSPSSL (SEQ ID NO: 33) | | 91.45% | 8.81E+06 |

TABLE 9-continued

Pharmaceutical potential detection and analysis: MS detection of humanized anti-human OX40 monoclonal antibodies after oxidative stress test

| Sample name | Peptide fragment | Sequence | Modification | Modification percentage | XIC area |
|---|---|---|---|---|---|
| AH02913-0h | C1-2 | DIQMTQSPSSL (SEQ ID NO: 33) | | | 1.54E+07 |
| AH02913-AAPH-24h | C18-19 | FCARVRPW (SEQ ID NO: 34) | Carbamidomethylation @2(96), oxidative @8(102) | 31.43% | 1.83E+05 |
| AH02913-AAPH-24h | C18-19 | FCARVRPW (SEQ ID NO: 34) | Carbamidomethylation @2(96) | 68.57% | 3.99E+05 |
| AH02913-0h | C18-19 | FCARVRPW (SEQ ID NO: 34) | Carbamidomethylation @2(96) | | 2.13E+06 |
| AH02913-AAPH-24h | C15-18 | MELSSLRSEDTAVYF (SEQ ID NO: 35) | Oxidative @1(81) | 7.31% | 2.54E+05 |
| AH02913-AAPH-24h | C15-18 | MELSSLRSEDTAVYF (SEQ ID NO: 35) | | 92.69% | 3.22E+06 |
| AH02913-0h | C15-18 | MELSSLRSEDTAVYF (SEQ ID NO: 35) | | | 6.43E+06 |
| AH02913-AAPH-24h | C71-72 | SCSVMHEALHNHY (SEQ ID NO: 36) | Carbamidomethylation @2(425), oxidative @5(428) | 52.17% | 1.55E+06 |
| AH02913-AAPH-24h | C71-72 | SCSVMHEALHNHY (SEQ ID NO: 36) | Carbamidomethylation @2(425), oxidative @5(428) | | 1.46E+06 |
| AH02913-AAPH-24h | C71-72 | SCSVMHEALHNHY (SEQ ID NO: 36) | Carbamidomethylation @2(425) | 47.835 | 2.76E+06 |
| AH02913-0h | C71-72 | SCSVMHEALHNHY (SEQ ID NO: 36) | Carbamidomethylation @2(425) | | 7.96E+06 |
| AH02916-AAPH-24h | C19 | CARVRPW (SEQ ID NO: 37) | Carbamidomethylation @1(96), oxidative @7(102) | 54.33% | 1.78E+05 |
| AH02916-AAPH-24h | C19 | CARVRPW (SEQ ID NO: 37) | Carbamidomethylation @1(96) | 45.67% | 1.50E+05 |
| AH02916-0h | C19 | CARVRPW (SEQ ID NO: 37) | Carbamidomethylation @1(96) | | 1.67E+06 |
| AH02916-AAPH-24h | C1-2 | DIQMTQSPSSL (SEQ ID NO: 33) | Oxidative @4(4) | 8.18% | 5.77E+05 |
| AH02916-AAPH-24h | C1-2 | DIQMTQSPSSL (SEQ ID NO: 33) | | 91.82% | 6.48E+06 |

TABLE 9-continued

Pharmaceutical potential detection and analysis: MS detection of humanized anti-human OX40 monoclonal antibodies after oxidative stress test

| Sample name | Peptide fragment | Sequence | Modification | Modification percentage | XIC area |
|---|---|---|---|---|---|
| AH02916-0h | | | | | |
| AH02916-AAPH-24h | C15-17 | MELSSLRSEDTAVY (SEQ ID NO: 35) | Oxidative @1(81) | 2.38% | 2.61E+05 |
| AH02916-0h | C15-16 | MELSSL (SEQ ID NO: 38) | | | 7.30E+05 |
| AH02916-AAPH-24h | C42-43 | MISRTPEVTCVVVDVSHEDPEVKF (SEQ ID NO: 39) | Oxidative @1(252), Carbamidomethylation @10(261) | 48.47% | 1.06E+06 |
| AH02916-AAPH-24h | C42-43 | MISRTPEVTCVVVDVSHEDPEVKF (SEQ ID NO: 39) | Carbamidomethylation @10(261) | 51.53% | 1.13E+06 |
| AH02916-0h | C41-42 | FPPKPKDTLMI (SEQ ID NO: 40) | | | 1.62E+06 |
| AH02916-AAPH-24h | C71-72 | SCSVMHEALHNHY (SEQ ID NO: 36) | Carbamidomethylation @2(425), oxidative @5(428) | 57.74% | 9.96E+05 |
| AH02916-AAPH-24h | C71-72 | SCSVMHEALHNHY (SEQ ID NO: 36) | Carbamidomethylation @2(425), oxidative @5(428) | | 9.81E+05 |
| AH02916-AAPH-24h | C71-72 | SCSVMHEALHNHY (SEQ ID NO: 36) | Carbamidomethylation @2(425) | 42.26% | 1.45E+06 |
| AH02916-0h | C71-72 | SCSVMHEALHNHY (SEQ ID NO: 36) | Carbamidomethylation @2(425) | | 4.56E+06 |
| AH02023-AAPH-24h | C21 | CARVRPW (SEQ ID NO: 37) | Carbamidomethylation @1(96), oxidative @7(102) | 35.78% | 3.25E+05 |
| AH02023-AAPH-24h | C21 | CARVRPW (SEQ ID NO: 37) | Carbamidomethylation @1(96) | 64.225 | 4.84E+05 |
| AH02023-0h | C21 | CARVRPW (SEQ ID NO: 37) | Carbamidomethylation @1(96) | | 1.83E+06 |
| AH02023-AAPH-24h | C1-2 | DIQMTQSPSSL (SEQ ID NO: 33) | Oxidative @4(4) | 9.56% | 1.06E+06 |
| AH02023-AAPH-24h | C1-2 | DIQMTQSPSSL (SEQ ID NO: 33) | | 90.44% | 1.00E+07 |
| AH02023-0h | C1-2 | DIQMTQSPSSL (SEQ ID NO: 33) | | | 1.35E+07 |
| AH02023-AAPH-24h | C73-74 | SCSVMHEALHNHY (SEQ ID NO: 36) | Carbamidomethylation @2(425), oxidative @5(428) | 58.23% | 1.74E+06 |

TABLE 9-continued

Pharmaceutical potential detection and analysis: MS detection of humanized anti-human OX40 monoclonal antibodies after oxidative stress test

| Sample name | Peptide fragment | Sequence | Modification | Modification percentage | XIC area |
|---|---|---|---|---|---|
| AH02023-AAPH-24h | C73-74 | SCSVMHEALHNHY (SEQ ID NO: 36) | Carbamidomethylation @2(425), oxidative @5(428) | | 1.64E+06 |
| AH02023-AAPH-24h | C73-74 | SCSVMHEALHNHY (SEQ ID NO: 36) | Carbamidomethylation @2(425) | 41.77% | 2.42E+06 |
| AH02023-0h | C73-74 | SCSVMHEALHNHY (SEQ ID NO: 36) | Carbamidomethylation @2(425) | | 6.21E+06 |
| AH02023-AAPH-24h | C6-8 | VRQAPGQGLEWMGW (SEQ ID NO: 41) | Oxidation @12(48) | 11.30% | 1.63E+05 |
| AH02023-AAPH-24h | C6-8 | VRQAPGQGLEWMGW (SEQ ID NO: 41) | | 88.70% | 1.28E+06 |
| AH02023-0h | C6-8 | VRQAPGQGLEWMGW (SEQ ID NO: 41) | | | 1.40E+06 |

TABLE 10

Pharmaceutical potential detection and analysis: MS detection of humanized anti-human OX40 monoclonal antibodies after deamidization stress test

| Sample name | Peptide fragment | Sequence | Modification | Modification percentage | XIC area |
|---|---|---|---|---|---|
| AH02913-0h | | | | | |
| AH02913-PH9.0-48h | | | | | |
| AH02916-0h | | | | | |
| AH02916-PH9.0-48h | | | | | |
| AH02023-0h | T91-93 | NQVSLTCLVK (SEQ ID NO: 42) | Carbamidomethylation @7(367) | 100.00% | 1.95E+07 |
| AH02023-PH9.0-48h | T91-93 | NQVSLTCLVK (SEQ ID NO: 42) | Carbamidomethylation @7(367) | 99.10% | 1.78E+07 |
| | T91-93 | NQVSLTCLVK (SEQ ID NO: 42) | Deamidization @1(361), carbamidomethylation @7(367) | 0.90% | 1.61E+05 |

What is claimed is:

1. A humanized anti-human OX40 monoclonal antibody or a functional fragment thereof, comprising a heavy chain variable region and a light chain variable region, wherein the heavy chain variable region comprises amino acid sequences as shown in the following HCDR1, HCDR2 and HCDR3 sequences, and the light chain variable region comprises amino acid sequences as shown in the following LCDR1, LCDR2 and LCDR3 sequences:
   HCDR1 having an amino acid sequence of DYSMH (SEQ ID NO: 27);
   HCDR2 having an amino acid sequence of WISTETGEPTYADDFKG (SEQ ID NO: 28);
   HCDR3 having an amino acid sequence of VRPWYLAV (SEQ ID NO: 29);
   LCDR1 having an amino acid sequence of RASQDISNYLN (SEQ ID NO: 30);
   LCDR2 having an amino acid sequence of YTSRLYS (SEQ ID NO: 31); and
   LCDR3 having an amino acid sequence of QQANTLPLT (SEQ ID NO: 32).

2. The humanized anti-human OX40 monoclonal antibody or a functional fragment thereof according to claim 1, wherein the amino acid sequence of the heavy chain variable region is selected from SEQ ID NO: 7, SEQ ID NO: 8, SEQ ID NO: 9, SEQ ID NO: 10, SEQ ID NO: 11, SEQ ID NO: 12, SEQ ID NO: 15 or SEQ ID NO: 16.

3. The humanized anti-human OX40 monoclonal antibody or a functional fragment thereof according to claim 1, wherein the amino acid sequence of the light chain variable region is selected from SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 or SEQ ID NO: 26.

4. The humanized anti-human OX40 monoclonal antibody or a functional fragment thereof according to claim 1, wherein the heavy chain variable region and the light chain variable region are selected from a combination of
   a heavy chain variable region as shown in SEQ ID NO: 7 and a light chain variable region as shown in SEQ ID NO: 17;
   a heavy chain variable region as shown in SEQ ID NO: 8 and a light chain variable region as shown in SEQ ID NO: 18;
   a heavy chain variable region as shown in SEQ ID NO: 9 and a light chain variable region as shown in SEQ ID NO: 19;
   a heavy chain variable region as shown in SEQ ID NO: 10 and a light chain variable region as shown in SEQ ID NO: 20;
   a heavy chain variable region as shown in SEQ ID NO: 11 and a light chain variable region as shown in SEQ ID NO: 21;
   a heavy chain variable region as shown in SEQ ID NO: 12 and a light chain variable region as shown in SEQ ID NO: 22
   a heavy chain variable region as shown in SEQ ID NO: 15 and a light chain variable region as shown in SEQ ID NO: 25; or
   a heavy chain variable region as shown in SEQ ID NO: 16 and a light chain variable region as shown in SEQ ID NO: 26.

5. The humanized anti-human OX40 monoclonal antibody or a functional fragment thereof according to claim 1, having a dissociation constant KD less than 3 nM with OX40.

6. An isolated polynucleotide, encoding the humanized anti-human OX40 monoclonal antibody or a functional fragment thereof according to claim 1.

7. The polynucleotide according to claim 6, comprising a heavy chain coding sequence encoding the heavy chain variable region of the humanized anti-human OX40 monoclonal antibody, and a light chain coding sequence encoding the light chain variable region of the humanized anti-human OX40 monoclonal antibody.

8. An expression vector, comprising the polynucleotide according to claim 6.

9. A host cell, comprising the expression vector according to claim 8.

10. A method of treating tumor or cancer in a subject in need thereof, comprising administering to the subject the humanized anti-human OX40 monoclonal antibody or a functional fragment thereof according to claim 1.

11. An anti-tumor pharmaceutical composition, comprising an effective amount of the humanized anti-human OX40 monoclonal antibody or a functional fragment thereof according to claim 1, and a pharmaceutically acceptable carrier.

12. A method for preparing the humanized anti-human OX40 monoclonal antibody or a functional fragment thereof according to claim 1, comprising:
   (1) humanizing the murine antibody, and obtaining variable region coding sequences of the light chain and the heavy chain of the humanized anti-human OX40 monoclonal antibody or a functional fragment thereof; and
   (2) using the variable region coding sequences in recombinant antibody production to obtain the functional humanized anti-human OX40 monoclonal antibody or a functional fragment thereof.

13. A method of treating tumor or cancer in a subject in need thereof, comprising administering to the subject the polynucleotide according to claim 6.

14. An anti-tumor pharmaceutical composition, comprising an effective amount of the humanized anti-human OX40 monoclonal antibody or a functional fragment thereof according to claim 4, and a pharmaceutically acceptable carrier.

15. A humanized anti-human OX40 monoclonal antibody or a functional fragment thereof, wherein the heavy chain variable region and the light chain variable region are selected from a combination of
   a heavy chain variable region as shown in SEQ ID NO: 13 and a light chain variable region as shown in SEQ ID NO: 23; or
   a heavy chain variable region as shown in SEQ ID NO: 14 and a light chain variable region as shown in SEQ ID NO: 24.

* * * * *